US012675291B2

(12) United States Patent
Aggarwal et al.

(10) Patent No.: US 12,675,291 B2
(45) Date of Patent: Jul. 7, 2026

(54) SYSTEM AND METHOD FOR DETERMINING COMMUNICATION PATHWAY

(71) Applicant: CareMetx, LLC, Bethesda, MD (US)

(72) Inventors: Naresh Aggarwal, Oak Park, CA (US); Mohd Nasir Ali, Southlake, TX (US); Matthew Hoffman, Bluffton, SC (US); James C. Rowe, III, Sugar Hill, GA (US); Karen Jeanne Tirozzi, Boston, MA (US)

(73) Assignee: CareMetx, LLC, Bethesda, MD (US)

( * ) Notice: Subject to any disclaimer, the term of this patent is extended or adjusted under 35 U.S.C. 154(b) by 80 days.

(21) Appl. No.: 18/478,631

(22) Filed: Sep. 29, 2023

(65) Prior Publication Data

US 2024/0120054 A1    Apr. 11, 2024

Related U.S. Application Data

(60) Provisional application No. 63/414,831, filed on Oct. 10, 2022.

(51) Int. Cl.
  G16H 40/67         (2018.01)
  G06N 20/00         (2019.01)
       (Continued)

(52) U.S. Cl.
  CPC ............. G16H 40/67 (2018.01); G06N 20/00 (2019.01); G16H 10/20 (2018.01); G16H 10/60 (2018.01);
       (Continued)

(58) Field of Classification Search
  CPC ......... G16H 10/60; G16H 20/10; G16H 80/00
       (Continued)

(56) References Cited

U.S. PATENT DOCUMENTS 2,555,327 A      6/1951   Elliott
2,818,494 A     12/1957   Bernard et al.
       (Continued)

FOREIGN PATENT DOCUMENTS

WO      WO-2015109167 A1 *  7/2015   ............. G06Q 10/10
WO      2020123106          6/2020

OTHER PUBLICATIONS

Linda D. Bosserman et al. ; Integrating Academic and Community Cancer Care and Research through Multidisciplinary Oncology Pathways for Value-Based Care: a Review and the City of Hope Experience; J. Clin. Med. 2021, 10, 188. https://doi.org/10.3390/jcm10020188 (Year: 2021).*
       (Continued)

*Primary Examiner* — Hiep V Nguyen
(74) *Attorney, Agent, or Firm* — Schwegman Lundberg & Woessner, P.A.

(57)         ABSTRACT

Systems and methods for providing an intelligent network to onboard patients to specialty medications are described herein. A server system for managing communication is configured to receive from a user at a healthcare practice, an electronic request to obtain a medical prior authorization (medPA) for a specialty drug to administer for a patient of the healthcare practice; select, using a rules service, a communication pathway to submit the medPA to a healthcare payer from a plurality of communication pathways; and initiate a connection with the healthcare payer using the selected communication pathway.

23 Claims, 15 Drawing Sheets

(51) Int. Cl.

| | |
|---|---|
| *G16H 10/20* | (2018.01) |
| *G16H 10/60* | (2018.01) |
| *G16H 20/10* | (2018.01) |
| *G16H 20/17* | (2018.01) |
| *G16H 40/20* | (2018.01) |
| *G16H 70/20* | (2018.01) |
| *G16H 80/00* | (2018.01) |

(52) U.S. Cl.
CPC ............. *G16H 20/10* (2018.01); *G16H 20/17* (2018.01); *G16H 40/20* (2018.01); *G16H 80/00* (2018.01); *G16H 70/20* (2018.01)

(58) Field of Classification Search
USPC .......................................................... 705/3
See application file for complete search history.

(56) References Cited

U.S. PATENT DOCUMENTS

| | | | |
|---|---|---|---|
| 6,021,392 | A | 2/2000 | Lester et al. |
| 6,859,780 | B1 | 2/2005 | Cunningham |
| 7,111,780 | B2 | 9/2006 | Broussard et al. |
| 7,438,218 | B2 | 10/2008 | Dooley et al. |
| 7,706,915 | B2 | 4/2010 | Mohapatra et al. |
| 7,716,068 | B2 | 5/2010 | Ball et al. |
| 7,720,569 | B2 | 5/2010 | Forrester et al. |
| 7,765,110 | B1 | 7/2010 | Koneru |
| 7,840,424 | B2 | 11/2010 | Wiley, II et al. |
| 7,856,364 | B1 | 12/2010 | Wiley, II et al. |
| 7,926,709 | B1 | 4/2011 | Dooley et al. |
| 7,957,983 | B2 | 6/2011 | Hoffman et al. |
| 7,979,285 | B2 | 7/2011 | Wiley et al. |
| 8,036,913 | B1 | 10/2011 | Pinsonneault et al. |
| 8,036,914 | B1 | 10/2011 | Pinsonneault |
| 8,036,918 | B1 | 10/2011 | Pinsonneault |
| 8,046,242 | B1 | 10/2011 | Dacosta et al. |
| 8,060,379 | B1 | 11/2011 | Pinsonneault et al. |
| 8,190,453 | B2 | 5/2012 | Rowe, III et al. |
| 8,219,418 | B2 | 7/2012 | Lilly et al. |
| 8,306,829 | B2 | 11/2012 | Starkey et al. |
| 8,386,274 | B1 | 2/2013 | Pinsonneault |
| 8,392,214 | B1 | 3/2013 | Pinsonneault |
| 8,392,219 | B1 | 3/2013 | Pinsonneault et al. |
| 8,566,117 | B1 | 10/2013 | Troutt et al. |
| 8,626,529 | B1 | 1/2014 | Pinsonneault |
| 8,682,697 | B1 | 3/2014 | Harris, Sr. |
| 8,762,163 | B1 | 6/2014 | Ringold |
| 8,781,854 | B1 | 7/2014 | Harris, Sr. |
| 8,924,231 | B2 | 12/2014 | Hoffman et al. |
| 9,177,340 | B2 | 11/2015 | Herzlinger |
| 9,779,217 | B2 | 10/2017 | Jordan et al. |
| 9,904,965 | B2 | 2/2018 | White et al. |
| 10,120,982 | B2 | 11/2018 | Jordan et al. |
| 10,157,262 | B1 | 12/2018 | Pinsonneault |
| 10,192,193 | B1 | 1/2019 | Glass |
| 10,242,337 | B2 | 3/2019 | Jordan et al. |
| 10,248,641 | B2 | 4/2019 | Wagh et al. |
| 10,417,380 | B1 | 9/2019 | Kaye et al. |
| 10,430,555 | B1 | 10/2019 | Pinsonneault, Sr. et al. |
| 10,489,552 | B2 | 11/2019 | Pinsonneault |
| 10,496,793 | B1 | 12/2019 | Lawrence et al. |
| 10,521,597 | B2 | 12/2019 | Reyes et al. |
| 10,616,146 | B1 | 4/2020 | Hopkins et al. |
| 10,642,957 | B1 | 5/2020 | Pinsonneault et al. |
| 10,956,386 | B2 | 3/2021 | Brown et al. |
| 10,958,601 | B2 | 3/2021 | Hopkins et al. |
| 10,978,198 | B1 | 4/2021 | Pinsonneault |
| 11,120,396 | B2 | 9/2021 | White et al. |
| 11,185,473 | B1 | 11/2021 | Warner |
| 11,334,822 | B2 | 5/2022 | Long et al. |
| 11,545,248 | B1 | 1/2023 | Nambirajan et al. |
| 2006/0259363 | A1 | 11/2006 | Jhetam |
| 2010/0082367 | A1 | 4/2010 | Hains et al. |
| 2010/0142692 | A1* | 6/2010 | Gotta .................... G16H 40/67 379/201.02 |
| 2011/0307274 | A1 | 12/2011 | Thompson et al. |
| 2012/0016687 | A1 | 1/2012 | Dhavle et al. |
| 2012/0253849 | A1 | 10/2012 | Parker et al. |
| 2013/0179177 | A1 | 7/2013 | Dhavle et al. |
| 2013/0191136 | A1 | 7/2013 | Apshago et al. |
| 2013/0325505 | A1 | 12/2013 | Vengco |
| 2014/0288945 | A1 | 9/2014 | Boerner et al. |
| 2014/0316796 | A1 | 10/2014 | Cox |
| 2015/0012289 | A1 | 1/2015 | Ben |
| 2015/0213202 | A1 | 7/2015 | Amarasingham et al. |
| 2015/0228030 | A1 | 8/2015 | Scantland et al. |
| 2015/0242583 | A1 | 8/2015 | Edson |
| 2015/0356272 | A1 | 12/2015 | Li et al. |
| 2016/0055314 | A1 | 2/2016 | Anderson et al. |
| 2016/0110523 | A1 | 4/2016 | Francois |
| 2016/0210636 | A9 | 7/2016 | Schoenberg |
| 2018/0181712 | A1 | 6/2018 | Ensey et al. |
| 2018/0293358 | A1 | 10/2018 | Sooudi et al. |
| 2018/0308569 | A1 | 10/2018 | Luellen |
| 2019/0102411 | A1* | 4/2019 | Hung .................... G06N 5/025 |
| 2019/0187690 | A1* | 6/2019 | Cella ................ G05B 19/41845 |
| 2019/0214116 | A1 | 7/2019 | Eberting |
| 2019/0244683 | A1 | 8/2019 | Francois |
| 2019/0372797 | A1* | 12/2019 | Ansari .................. H04L 67/104 |
| 2020/0020428 | A1 | 1/2020 | Avery et al. |
| 2020/0066387 | A1 | 2/2020 | Pullabhatla et al. |
| 2020/0203015 | A1* | 6/2020 | Weinstein .............. G16H 10/60 |
| 2020/0250203 | A1 | 8/2020 | Calco et al. |
| 2021/0005303 | A1 | 1/2021 | Mercier et al. |
| 2021/0151155 | A1 | 5/2021 | Dana et al. |
| 2021/0158924 | A1* | 5/2021 | Stueckemann ........ G16H 40/60 |
| 2021/0200896 | A1 | 7/2021 | Lilja et al. |
| 2021/0295971 | A1 | 9/2021 | Mills et al. |
| 2021/0312512 | A1* | 10/2021 | Sampson .............. G06Q 40/08 |
| 2021/0319887 | A1 | 10/2021 | Derrick, Jr. et al. |
| 2022/0005558 | A1 | 1/2022 | Malfait et al. |
| 2022/0254466 | A1 | 8/2022 | Hwang et al. |
| 2022/0292474 | A1 | 9/2022 | Littell |
| 2022/0415464 | A1 | 12/2022 | Dana et al. |
| 2023/0196471 | A1 | 6/2023 | Mendell et al. |
| 2024/0005361 | A1 | 1/2024 | Jain |
| 2024/0120074 | A1 | 4/2024 | Aggarwal et al. |
| 2024/0120090 | A1 | 4/2024 | Lens-Ter Berg et al. |
| 2025/0191750 | A1 | 6/2025 | Aggarwal et al. |

OTHER PUBLICATIONS

U.S. Appl. No. 18/357,031, filed Jul. 21, 2023, System and Method for Enrollment Into Patient Service Programs.

U.S. Appl. No. 18/478,652, filed Sep. 29, 2023, System and Method for Automated Patient Engagement.

"U.S. Appl. No. 18/357,031, Non Final Office Action mailed Oct. 2, 2023", 17 pgs.

APIXIO, "Solving the Prior Authorization Problem With AI", White Paper—www.apixio.com, (Mar. 25, 2022), 9 pages.

Campbell, Kevin, "Using Patient Engagement Platforms in the Postoperative Management of Patients", Current Reviews in Musculoskeletal Medicine 13, (May 9, 2020), 6 pages.

Choudhry, Niteesh K, "Drug Company Sponsored Patient Assistance Programs a Viable Safety Net", Health Affairs vol. 28 No. 3, (Jun. 2009), 8 pages.

EDIFECS, "AI NLP for Realtime Prior Authorization for Payers and Providers", (Oct. 26, 2022), pp. 5, 6, 11.

Kirker, "Flagler Hospital improves revenue by helping self-pay patients", Flagler Hospital improved its financial assistance enrollment and eligibility program Revenue Cycle Strategist, (Sep. 2012), 4 pages.

Lobach, David F, "Integrating a Patient Engagement App into an Electronic Health Record-Enabled Workflow Using Interoperability Standards", Appl Clin Inform 13, (Dec. 14, 2022), 9 pages.

Nair, Navaneeth, "Managing Prior Authorizations with Artificial Intelligence", Compliance, Computing Systems, Information Technology, Lab Management, Middleware and Software, (Apr. 13, 2020), 10 pages.

Oconnor, Niall, "Reforming Prior Authorization with AI and Machine Learning", [Online]. Retrieved from the Internet: <https://insidebigdata.com/2022/07/07/reforming-prior-authorization-with-ai-and-machine-learning/ (Jul. 7, 2022), 4 pages.

(56)     References Cited

OTHER PUBLICATIONS

Udenyca, "Coherus Complete Reimbursement and Billing Guide", (May 23, 2019), 16 pages.

U.S. Appl. No. 18/357,031, Final Office Action mailed Jan. 24, 2024, 15 pgs.

U.S. Appl. No. 18/357,031, Response filed Dec. 29, 2023 to Non Final Office Action mailed Oct. 2, 2023, 12 pgs.

U.S. Appl. No. 18/478,652, Non Final Office Action mailed Jan. 24, 2024, 15 pgs.

Glasgow, et al., "The NUDGE trial pragmatic trial to enhance cardiovascular medication adherence: study protocol for a randomized controlled trial", randomized controlled trial, (Aug. 11, 2021), 31 pgs.

Som, et al., "A Novel Patient Engagement Platform Using Accessible Text Messages and Calls (Epharmix): Feasibility Study", JMIR Form Res, (Sep. 18, 2017), 9 pgs.

U.S. Appl. No. 18/357,031, Advisory Action mailed Apr. 5, 2024, 4 pgs.

U.S. Appl. No. 18/357,031, Amendment Filed Apr. 11, 2024, 11 pages.

U.S. Appl. No. 18/357,031, Response filed Mar. 25, 2024 to Final Office Action mailed Jan. 24, 2024, 12 pgs.

U.S. Appl. No. 18/478,652, Examiner Interview Summary mailed Apr. 3, 2024, 2 pgs.

U.S. Appl. No. 18/357,031, Notice of Allowability mailed Jul. 24, 2024, 2 pgs.

U.S. Appl. No. 18/357,031, Notice of Allowance mailed Jul. 11, 2024, 9 pgs.

U.S. Appl. No. 18/478,652, Response filed Jun. 3, 2024 to Non Final Office Action mailed Jan. 24, 2024, 12 pgs.

Safran, et al., "PERSIST Sensing Network: a Multimodal Sensing Network Architecture for Collection of Patient-Generated Health Data in the Clinical Workflow", IEEE, (2021).

U.S. Appl. No. 18/478,652, Response filed Nov. 14, 2024 to Final Office Action mailed Oct. 2, 2024, 8 pgs.

U.S. Appl. No. 18/478,652, Final Office Action mailed Oct. 2, 2024, 12 pgs.

U.S. Appl. No. 18/478,631, Supplemental Amendment filed Feb. 3, 2025, 11 pages.

U.S. Appl. No. 18/478,652, Advisory Action mailed Dec. 9, 2024, 5 pgs.

U.S. Appl. No. 18/478,652, Non Final Office Action mailed Feb. 3, 2025, 11 pgs.

U.S. Appl. No. 18/478,652, Response filed Aug. 4, 2025 to Non Final Office Action mailed Feb. 3, 2025, 13 pgs.

U.S. Appl. No. 18/893,819, Preliminary Amendment filed Jan. 26, 2025, 8 pages.

* cited by examiner

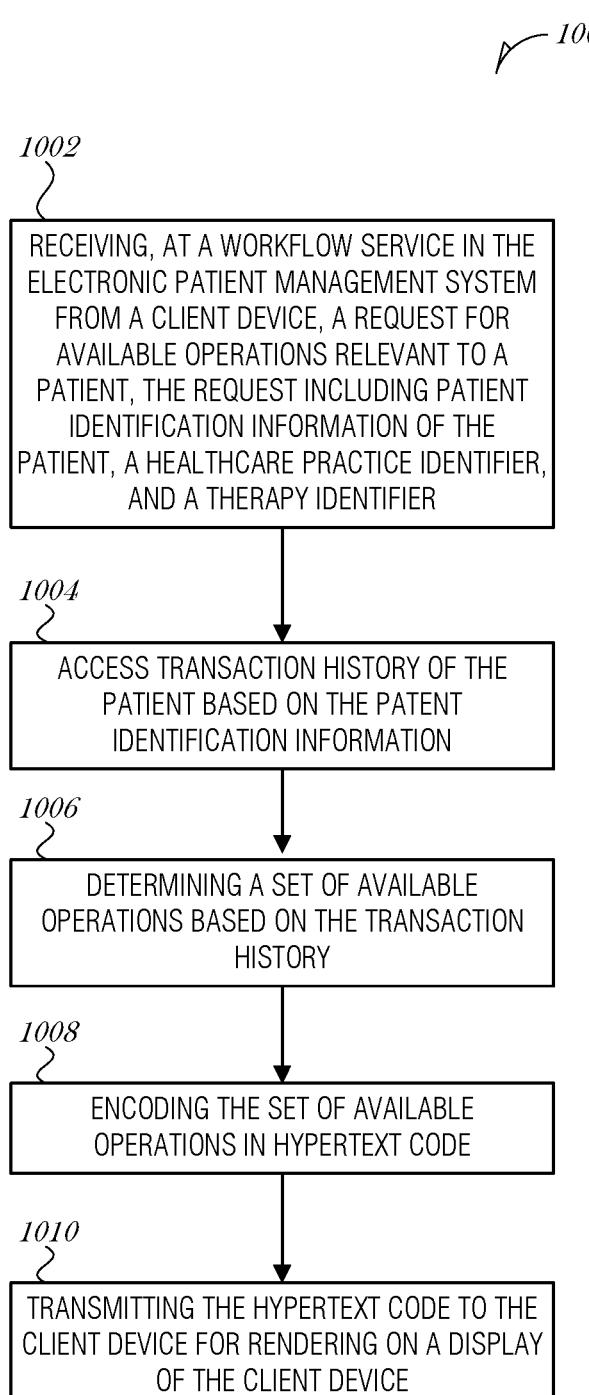

*1000*

*1002*

RECEIVING, AT A WORKFLOW SERVICE IN THE ELECTRONIC PATIENT MANAGEMENT SYSTEM FROM A CLIENT DEVICE, A REQUEST FOR AVAILABLE OPERATIONS RELEVANT TO A PATIENT, THE REQUEST INCLUDING PATIENT IDENTIFICATION INFORMATION OF THE PATIENT, A HEALTHCARE PRACTICE IDENTIFIER, AND A THERAPY IDENTIFIER

*1004*

ACCESS TRANSACTION HISTORY OF THE PATIENT BASED ON THE PATENT IDENTIFICATION INFORMATION

*1006*

DETERMINING A SET OF AVAILABLE OPERATIONS BASED ON THE TRANSACTION HISTORY

*1008*

ENCODING THE SET OF AVAILABLE OPERATIONS IN HYPERTEXT CODE

*1010*

TRANSMITTING THE HYPERTEXT CODE TO THE CLIENT DEVICE FOR RENDERING ON A DISPLAY OF THE CLIENT DEVICE

RECEIVE REQUEST FOR MEDPA

*1304*

SELECT COMMUNICATION PATHWAY TO
SUBMIT MEDPA TO PAYER

*1306*

INITIATE CONNECTION WITH PAYER USING
SELECTED COMMUNICATION PATHWAY

COMPUTE NODE — 1400

COMPUTE CIRCUITRY — 1402

PROCESSOR — 1404

MEMORY — 1406

I/O SUBSYSTEM — 1408

DATA STORAGE — 1410

COMM. CIRCUITRY SUBSYSTEM — 1412

NIC — 1420

PERIPHERAL DEVICE(S) — 1414

SYSTEM AND METHOD FOR DETERMINING COMMUNICATION PATHWAY

PRIORITY APPLICATION

This application claims the benefit of priority to U.S. Provisional Application Ser. No. 63/414,831, filed Oct. 10, 2022, which is incorporated herein by reference in its entirety.

TECHNICAL FIELD

Embodiments described herein generally relate to data communication and analysis systems and in particular to a system and method for determining communication pathways.

BACKGROUND

Patients with serious illnesses often require treatment with specialty medications. The process to gain approval to treat a patient with these medications is fractured, multi-step, and onerous for all involved parties, such as the patient, treating provider, insurance company, dispensing entity (pharmacy, specialty pharmacy, or distributor) and the manufacturer. Specialty medications, whether dispensed through a specialty pharmacy or by a provider via a buy-and-bill process, typically need to be approved by a patient's insurer before treatment. This may also involve investigation of a patient's insurance plan, coverage of the specific requested treatment, and often prior authorization of the treatment by the insurance plan. It should, but does not always, include an assessment of affordability of the treatment by the patient, including identifying various programs sponsored by the manufacturer of the treatment or other entities that may provide financial aid. In many cases of severe illness, additional supportive services are required, such as adherence or transportation supports, possibly offered by the manufacturer, the patient's health plan, or other prescribed digital therapeutics.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings in which:

FIG. 10 is a flowchart illustrating a method for onboarding patients into an electronic patient management system, according to an embodiment;

DETAILED DESCRIPTION

Figure 1:
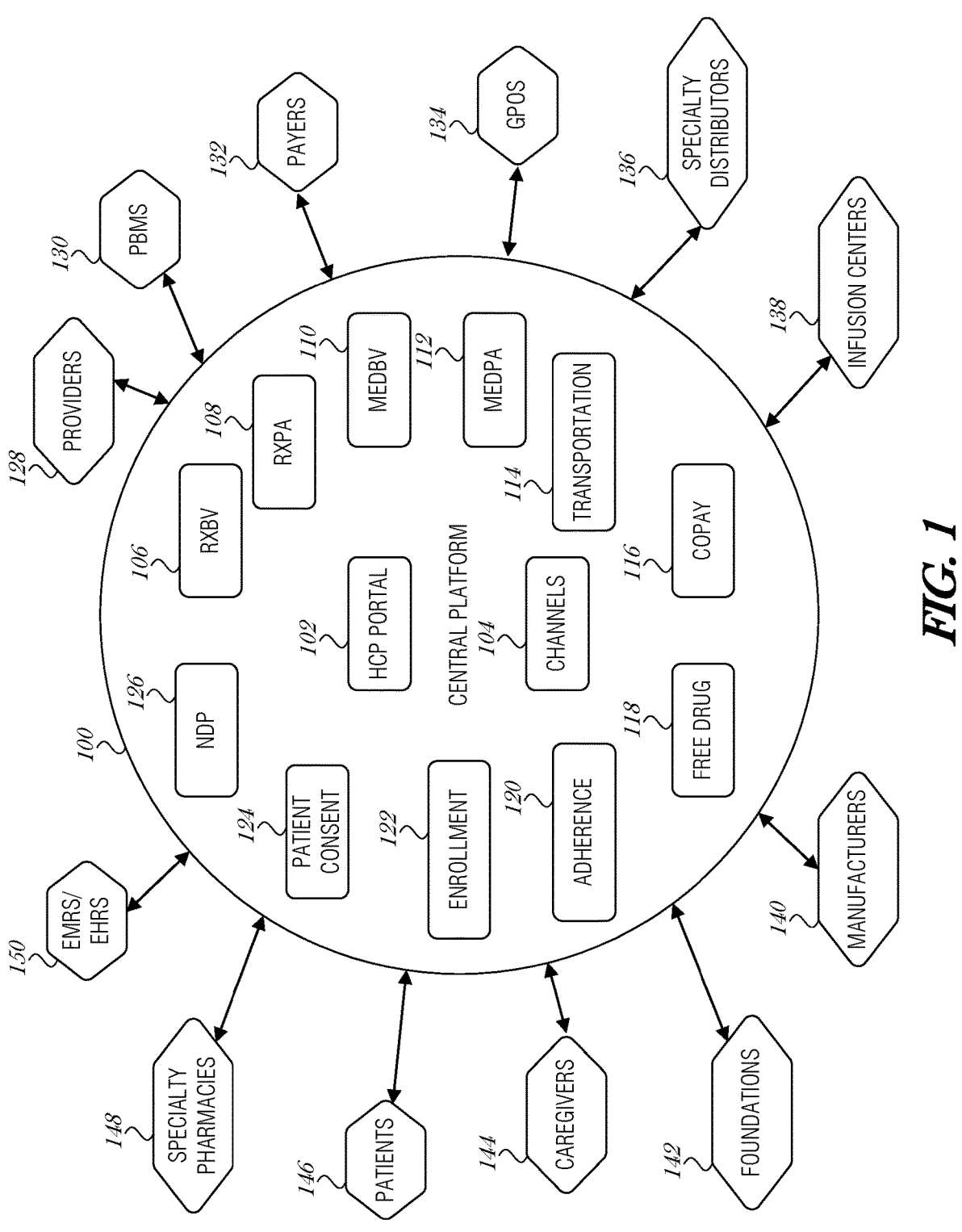
FIG. 1 is a diagram showing an overview of a central platform for patient management, according to an embodiment.

In the following description, for purposes of explanation, numerous specific details are set forth in order to provide a thorough understanding of various example embodiments. It will be evident, however, to one skilled in the art that the present disclosure may be practiced without these specific details.

In complex treatment scenarios, there is no single network to navigate the operations needed to start a patient on a prescribed therapy. The operations needed and tools available vary depending on whether the therapy is covered on a patient's medical benefit or pharmacy benefit portion of their health insurance.

For pharmacy benefit products (generally oral, inhaled, or self-injectable therapies), a patient or the prescriber can contact the patient's pharmacy benefit manager for eligibility, coverage, and patient financial responsibility information. Providers may also use an electronic medical record (EMR) or other software system to determine pharmacy-benefit eligibility and patient financial responsibility information. Prescribers are often left to determine the best and most expedient path to verify a patient's insurance and obtain coverage details for the specific therapy they are prescribing.

For prior authorization of these pharmacy-benefit therapies, providers may request such authorization in a number of ways, including calling the payer, submitting electronic queries via an NCPDP (National Council for Prescription Drug Programs) standard protocol, via a payer-specific web-based portal, or by faxing forms to the payer. However, because of the lack of standardization, there is no easy way to determine which methods are supported by the payer or which is the most expedient.

For medical benefit products, a patient or the prescriber can contact the patient's health plan provider for eligibility and coverage information. Beyond basic insurance eligibility information, no electronic network exists for coverage of specific therapies on the medical benefit, which generally include infused, provider-administered injectable, or implantable treatments. Providers are forced to contact the plan provider to learn coverage details, patient financial responsibility, and whether the provider can purchase the therapy or if it must be dispensed by a specialty pharmacy before administration. There is no electronic network for medical benefit drug coverage/benefit verification.

For prior authorization of medical benefit products, providers must contact the patient's health plan, utilize payer-specific web-based portals if supported by the payer, fax prior authorization forms to the payer if supported by the payer, or purchase the use of a small number of electronic tools in the market (e.g., Availity, Infinix, MyndShft, Sama-Care) to complete prior authorization forms digitally via robotic process automation (RPA) across multiple payer portals. However, as with the pharmacy benefits, there is no standardized or centralized platform to easily determine which methods are supported by the payer or which is the most expedient.

In sum, for both pharmacy and medical benefits, there is no centralized tool to identify patient services or other supported services specific to the therapy being prescribed. Patient service programs (also referred to as patient support programs) and other supported services include services to assist with insurance access and coverage issues, benefit verification or investigations, patient assistance (e.g., financial assistance), working with specialty pharmacies to provide treatment, coordinating infusion services, providing educational resources and patient advocacy, or providing product or treatment support. PSPs are often sponsored by a drug manufacturer, device manufacturer, therapy provider, etc. The result of these fractured processes generally means the onus to navigate these processes falls on the provider prescribing the therapy, causing delays in initiating treatment for the patient and administrative costs borne by the prescriber.

The systems and techniques described herein provide a central platform to manage the operations to determine coverage for the patient. The central platform leverages proprietary functions to streamline the process and provide an efficient outcome. The central platform provides a variety of services for managed medications on either the pharmacy or medical benefit. The services include benefit verification or investigation services, prior authorization services, patient engagement services, affordability services, prescription services, site of care management services, treatment referral services, and transportation services. These features and others are described in more detail below.

Additionally, the systems and techniques described herein provide a platform to manage prior authorization requests for specialty drugs. In conventional systems, prior authorization requests may go unresolved because a communication pathway is not functional, not monitored, or is otherwise deficient. In order to provide timely prior authorization results (e.g., a final disposition of a request to either an approval, an approval in part, or a denial), the central platform leverages heuristic analytics to streamline the prior authorization process. The platform analyzes a number of features, such as time to obtain prior authorization, the type or amount of data required for the prior authorization, follow up frequency, and the like, to determine a preferred communication pathway to attempt to obtain the prior authorization from the payer. The preferred communication pathway may be automatically initiated to further streamline the user's experience. These features and others are described in more detail below.

FIG. 1 is a diagram showing an overview of a central platform 100 for patient management, according to an embodiment. The central platform 100 includes a healthcare professional (HCP, also referred to as a healthcare provider) portal 102, one or more channels 104, an RxBV (prescription benefit verification) service 106, an RxPA (prescription prior authorization) service 108, a MedBV (medical benefit verification) service 110, a MedPA (medical prior authorization) service 112, a transportation assistance service 114, a copay service 116, a free drug service 118, an adherence service 120, an enrollment service 122, a patient consent service 124, and a non-dispensing pharmacy (NDP) service 126. It is understood that the central platform 100 may include more or fewer services than those illustrated in FIG. 1.

The services 106-126 provide a broad array of functions, such as benefit investigation and verification (e.g., using the RxBV 106 or MedBV 110 services), prior authorization checks (e.g., using the RxPA 108 or MedPA 112 services), prescription and electronic prescription (eRx) routing through a non-dispensing pharmacy (NDP) with the NDP service 126, and transactional status awareness, for example.

Additionally, the central platform 100 is used to connect various parties and systems that are involved with patient treatment, such as healthcare providers 128, PBMs (pharmacy benefit manager) 130, payers 132, GPOs (group purchasing organization) 134, specialty distributors 136, infusion centers 138, manufacturers 140, foundations 142, caregivers 144, patients 146, specialty pharmacies 148, and electronic medical/health record systems 150.

Pharmacy Benefit Managers (PBMs) 130 are insurers that specialize in managing covered pharmacy drugs for the prescription portion of a patient's health insurance plan. A group purchasing organization (GPO) 134 is an entity that helps healthcare providers realize savings and efficiencies by aggregating purchasing volume and using that leverage to negotiate discounts with manufacturers, distributors, and other vendors.

The central platform 100 provides end-to-end support to onboard a patient 146 to a specialty medication or other treatment as prescribed by a healthcare provider 128. This consolidated and integrated system addresses many of the disadvantages of known systems. The central platform 100 aggregates data across systems and applies workflows to streamline pathways to initiate therapy for a patient and optimize outcomes for stakeholders (e.g., providers 128, GPO 134, PBMs 130, etc.).

The central platform 100 may add value to healthcare providers 128 by decreasing burden during the prescribing process. This allows for faster patient onboarding with lower costs. The central platform 100 acts as a single source of the status of various transactions involving specialty medication or treatment onboardings. The central platform 100 also provides increased visibility and awareness of support services, including adherence, transportation, and affordability options for the patient.

The central platform 100 may add value for payers 132 (e.g., insurance companies) by providing standardized protocols for communicating coverage details and prior authorization requests. This expedites appropriate approvals and lowers costs through the approval process. The central platform 100 also increases visibility for adherence or other clinical programs offered by the payer 132.

The central platform 100 may add value for patients 146 by providing reduced waiting before beginning therapy, access to supportive services through a simple integrated portal, and transparency in the onboarding process. The patients 146 may access the central platform 100 through one or more channels 104. Channels 104 are electronic, telephonic, and other communication pathways for patients to interact with the central platform 100. Channels 104 may be supported directly by the central platform 100 or by way of a partner. A partner is one that may contract with the central platform 100 to provide an intermediary service for patients to interact with the central platform 100. Partners may develop their own independent software platforms to provide unique or specialized services offered exclusively by the partner to the patients 146. An application programming interface (API) may be provided by the central platform 100 to partners in order for the partner to access services and data hosted by the central platform 100.

The central platform 100 may add value for manufacturers 140, as well, by standardizing the process to onboard patients 146 to prescribed specialty medications, and reducing the time to market. Manufacturers 140 can also use the central platform 100 to increase visibility for adherence service 120 or other clinical programs offered by the manufacturer 140.

Figure 2:
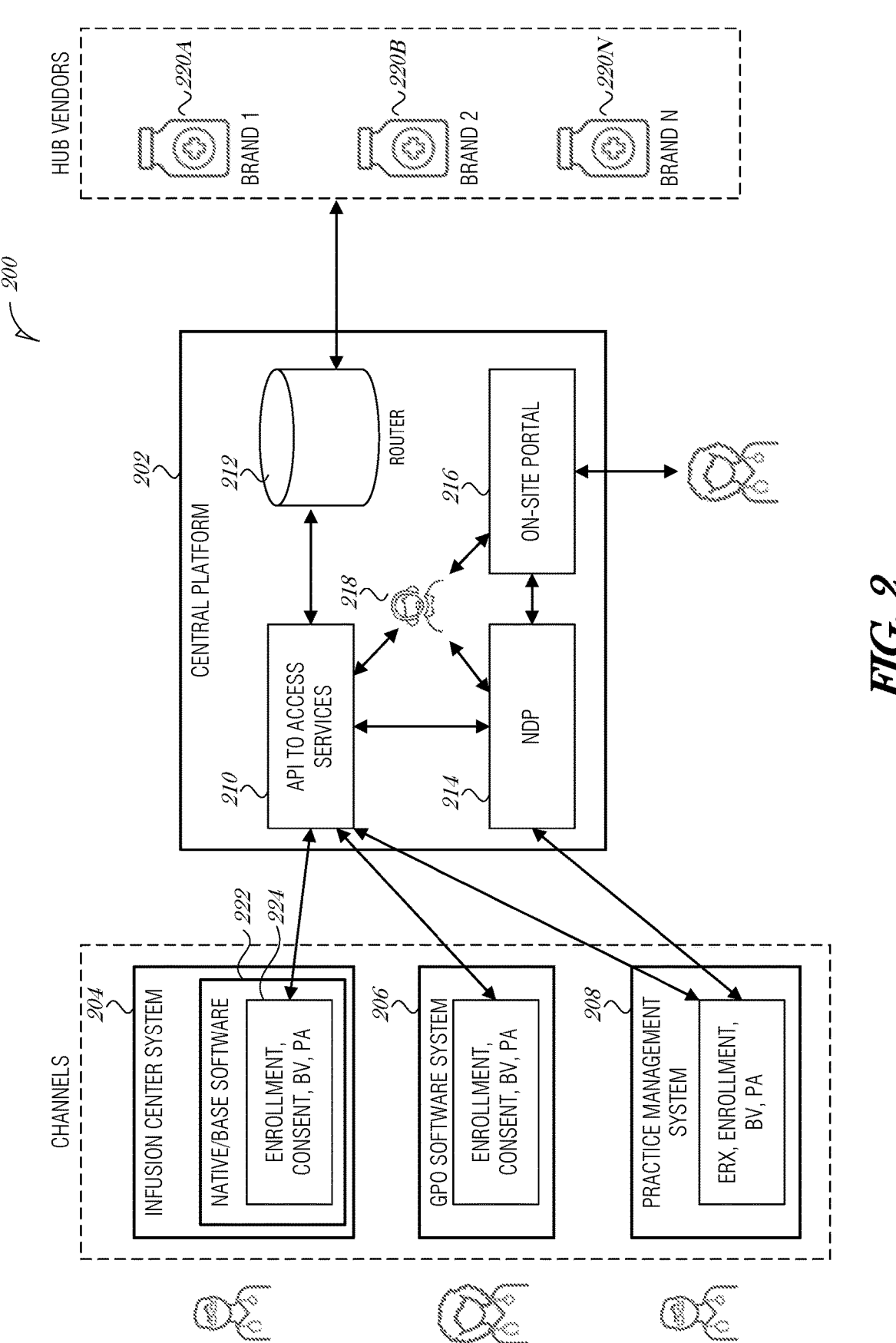
FIG. 2 illustrates an operating environment, according to an embodiment.

FIG. 2 illustrates an operating environment 200, according to an embodiment. A central platform 202 is used to provide services to various channels (e.g., different ways to access the central platform 202) and partners (e.g., businesses that develop complimentary platforms to interface with the central platform 202), including an infusion center system 204, a GPO software system 206, and a practice management system 208. The systems 204, 206, and 208 can access the central platform to obtain information about enrollment, patient consent, benefit verification, prior authorizations, prescription information, and the like. Additionally, vendors 220A-N (e.g., manufacturers) may access the central platform.

The central platform 202 provides an application programming interface (API) to access services 210, a data store 212, a non-dispensing pharmacy (NDP) 214, an on-site portal 216, and on-site operators 218. Within central platform 202, the API to access services 210 acts as the single endpoint for stakeholder connections and uses business rules that provide efficient brokerage of each transaction. The central platform 202 is able to communicate the status of each transaction back to the end user, allowing the user to see the statuses for different transactions, which may be performed by different stakeholders (e.g., payer, specialty pharmacy, manufacturer sponsored hub service).

Business rules within the API to access services 210 enable different transactions or microservices. These rules are used to determine coverage, prior authorization requirements, and out of pocket expenses for the patient. Rules are also used to facilitate therapy initiation, such as additional affordability options (e.g., manufacturer-sponsored free drug programs, foundation-supported programs, etc.), transportation options (e.g., payer-sponsored options) and adherence or persistence supports (e.g., manufacturer, payer, or foundation supported programs).

Partners are groups or organizations that partner with the owner or primary business of the central platform 202. Partners develop software solutions that may be offered to end users (e.g., medical practices, healthcare providers, insurance providers, and the like). The software solutions provided by partners may be used in conjunction with services and solutions provided by the central platform 202. For instance, the central platform 202 may offer a generic version of a service and the partner may offer a tailored version of the service to the same end user. The partners are able to use some or all of the services offered by the central platform 202. These services may be sold to the partners using different models (e.g., an annual license). In the example illustrated in FIG. 2, partners may develop and provide the GPO software system 206 or the practice management system 208. The partner's system is able to access the central platform 202 via the API to access services 210. The UI hosted by the central platform 202 may be integrated seamlessly into the UI of the partner software, which provides a consistent look and feel and easier interface for the end user.

In another example, a partner may provision a software platform to the infusion center system 204. A user at the infusion center system 204 may use base software 222 that is provided by their own information services department (e.g., native software). The base software 222 may include a web browser (e.g., GOOGLE CHROME, APPLE SAFARI, FIREFOX, etc.) and the partner's software platform. The partner's software platform may be installed as a plug-in to the web browser or may be accessible over the network, such as at an access-controlled website. The base software 222 along with the partner software is used to access the API to access services 210 using an embedded user interface 224 (UI) within the base software 222. Calls to the central platform 202 via the API are performed using Hypertext Transfer Protocol (HTTP) messaging protocols, such as with Simple Object Access Protocol (SOAP) or Representational State Transfer (REST). This modular approach allows partners to selectively embed only the services and transactions that they need. Additionally, the use of embedded user interfaces allows for a consistent look and feel to the end user. This reduces potential consumer confusion during navigating and using the service.

Figure 3:
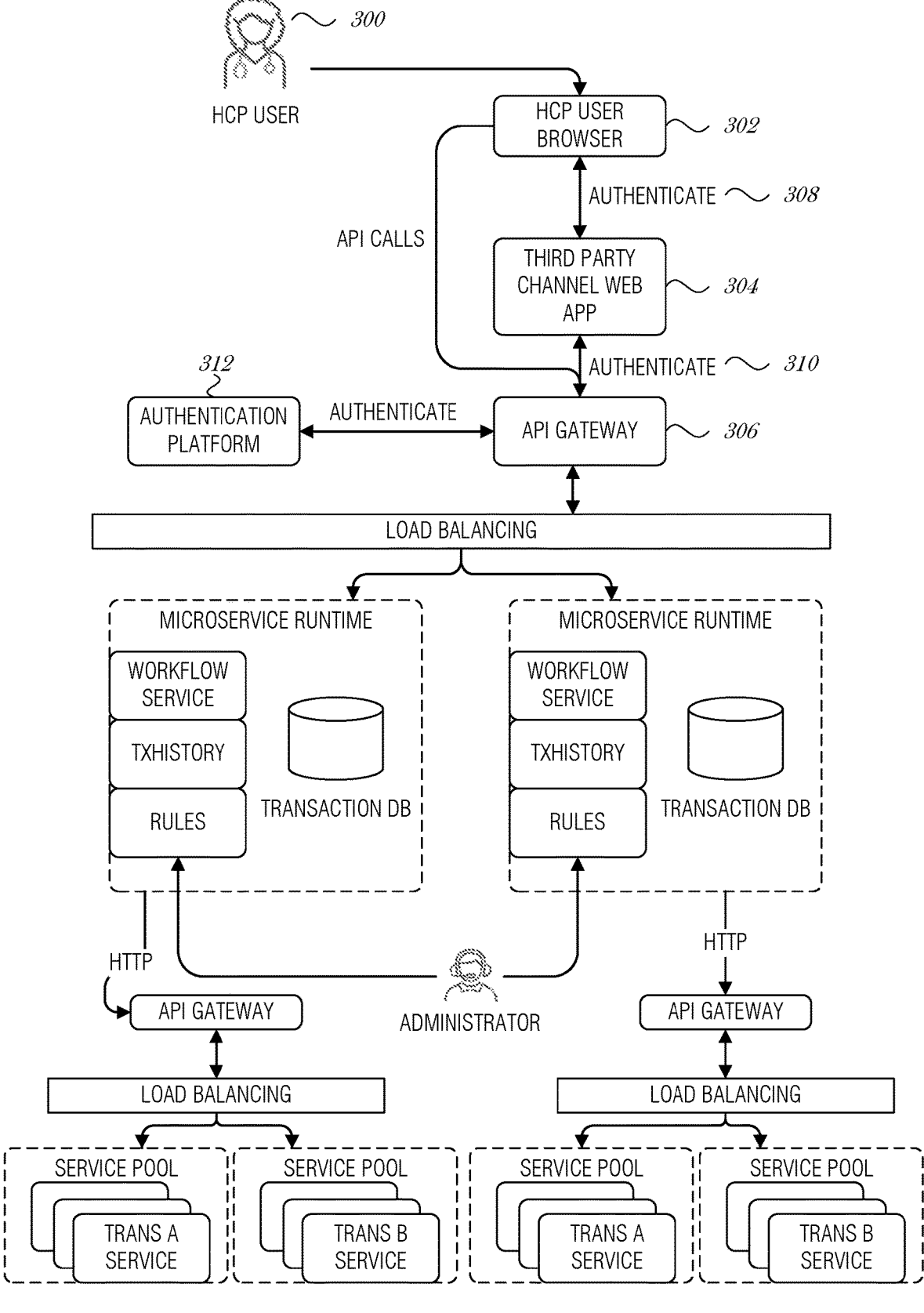
FIG. 3 is a diagram illustrating control and data flow, according to an embodiment.

FIG. 3 is a diagram illustrating control and data flow, according to an embodiment. A healthcare professional (HCP) user 300 accesses a native practice management platform via a web browser 302. The web browser 302 executes client-side software development kit (SDK) tools to interact with an API gateway 306. The client-side SDK may include JavaScript components. The web browser 302 authenticates with the native platform 304 (operation 308), which may be a web application. The native platform 304 may authenticate to the API gateway 306 (operation 310). Authentication at the API gateway 306 may be handled by an identity authentication platform 312 (e.g., Okta).

The API gateway 306 may be implemented using a cloud service provider (CSP), such as Amazon Web Services (AWS). A middleware vendor, such as WSO2, may be used on the CSP to efficiently design, deploy and maintain APIs. WSO2 is an open-source technology provider founded in 2005. It offers an enterprise platform for integrating application programming interfaces (APIs), applications, and web services locally and across the Internet.

One or more layers of microservices may be implemented with load balancing, in various embodiments, to provide a full suite of services to the HCP user 300. Microservices may execute other microservices in a hierarchical manner.

Microservices may be distributed across hosting regions with no shared points of failure for any one functional fault domain. This provide redundancy and resiliency, meaning no two microservices can share the same host, virtual machine (VM), disk, or compute resource. Services are redundant across network resources meaning regionally redundant and accessed by separate circuits. All components within an execution path are monitored by application performance monitoring tools.

Figure 4:
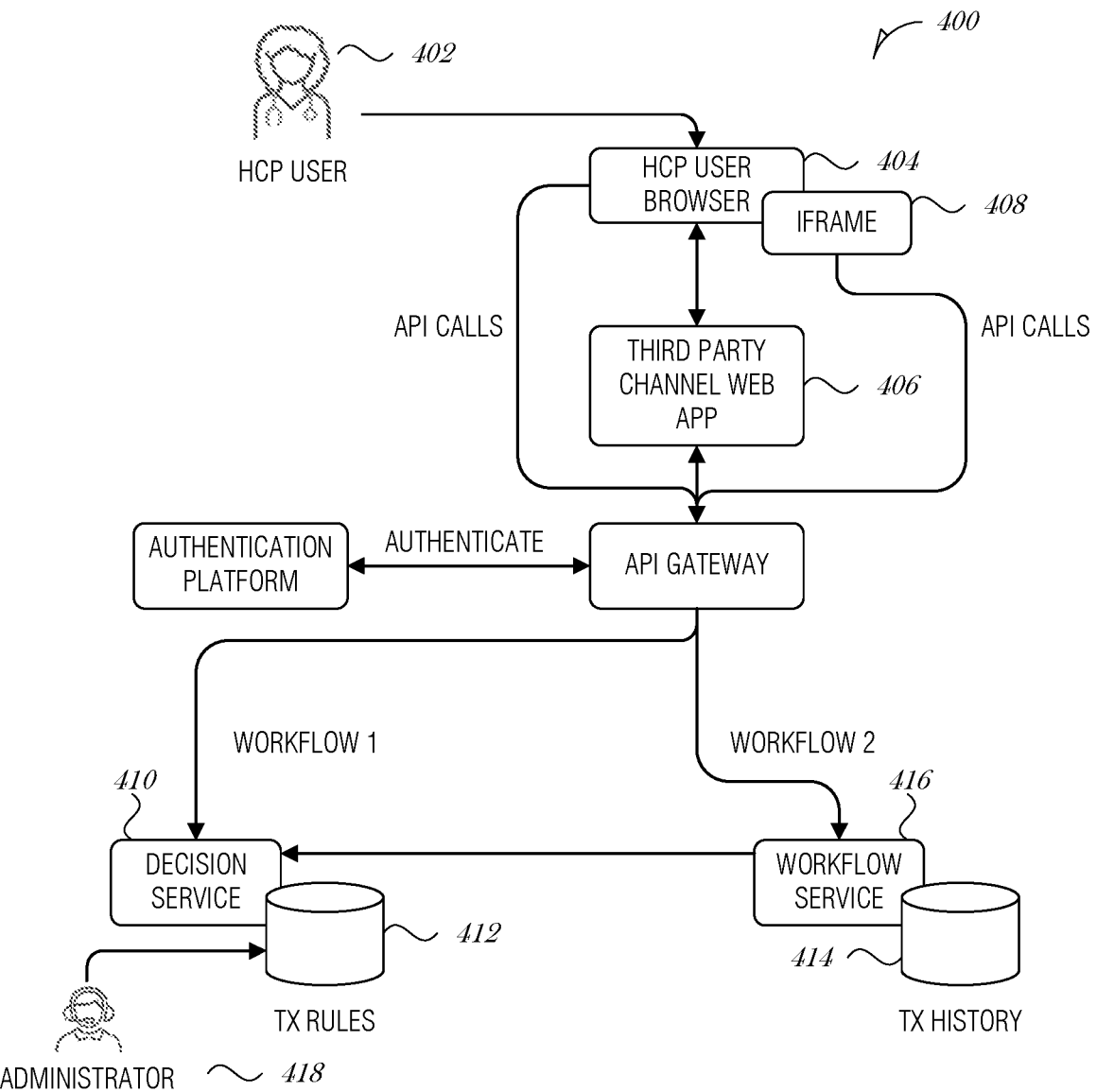
FIG. 4 is another diagram illustrating control and data flow, according to an embodiment.

FIG. 4 is another diagram illustrating control and data flow 400, according to an embodiment. The control and data flow 400 enables a calling client device to determine which transactions are available for a given patient and therapy. The available transactions may be used by the client device to generate a menu in a native user experience layer (e.g., native platform UI). The menu is of available transactions provided by a central platform, which is different than the native platform of the HCP user.

An HCP user 402 uses a browser interface 404 to access a native web app platform 406. An embedded element 408 in the browser interface 404 is used to provide options or a menu of the transactions available from the central platform. The embedded element 408 may be a <DIV> element or an <IFRAME> element in an HTML document.

In a first workflow, a request may be provided via the embedded element 408 to obtain a list of actions that are allowed for a given transaction identifier (ID). The request may take the form:

GET:/API/Access/Patients/{PartnerPatientID}/Actions where the Body element includes {Patient, Drug, PartnerPatientID}. The Patient variable may be identifying information, such as first name, last name, date of birth, social security number, unique identifier, etc. The PartnerPatientID is a unique patient ID for the partner. The PartnerPatientID is used in combination with the patient ID and drug to uniquely identify the transaction (e.g., does the patient need an enrollment).

A decision service 410 uses rules in a transaction rules database 412 to determine which actions/transactions are available given a transaction identifier and transaction history. The transaction history is stored in a transaction history database 414 and is accessible via a workflow service 416. The available actions/transactions are returned as URLs for rendering in the client browser interface 404.

In a second workflow, a request may be provided via the embedded element 408 to obtain a menu of actions that are allowed given a partner client identifier (ID). The request may take the form:

GET:/API/Access/Patients/{PartnerPatientID}/Actions/Menu and the response may be in the form of embeddable HTML that renders a menu of actions.

The workflow service 416 interfaces with the decision service 410 to obtain available workflow operations given a transaction history and status.

To determine the transactions that are available to the HCP user 402 at a given time, the service uses a transaction history to identify available workflow operations. The workflow operations are provided by an administrator user 418 who inputs the business rules that control when workflows are available.

The microservices can be accessed by the API or other proprietary modules (e.g., UI frontends to APIs). This provides an embedded UI to partners. The modular approach allows network partners to embed only the services/transactions that fulfill their particular needs.

As an example, a tablet-based platform that supports visually impaired retina patients to digitally check into appointments may extend its digital enrollment capability by using the API to include initiation of additional access services for the HCPs treating these patients. The embedded functionality speeds up access to therapy and lowers the burden on the HCP at the same time. It also extends the partner's pre-existing enrollment services to include an eBV (electronic benefit verification) service from the central platform (e.g., RxBV service 106 or MedBV service 110 of central platform 100).

As another example, a retina therapy-focused GPO may have a robust solution to help their HCP customers manage drug inventory and costs, but it may not have the ability for their users to see if a patient is covered for a therapy the provider wants to purchase to treat the patient. The central platform's enrollment, benefit verification, and prior authorization capabilities can all be made available in the partner system to consolidate workflows needed to initiate therapies acquired under a buy-and-bill scenario.

As another example, a platform that specializes in prior authorization may want to offer additional access services to its user base, such as enrollment and medical eBV services. The central platform's services API may be used to extend the partner's pre-existing service of prior authorization to include enrollment and eBV transactions/microservices.

As another example, a software platform supporting infusion center management may have robust capabilities to order therapies and manage patient schedules, but may not have to ability to verify benefits, initiate prior authorization, or access manufacturer-sponsored programs on the patient's behalf. The central platform's enrollment, benefit verification, and prior authorization capabilities can all be made available in the partner system to consolidate workflows needed to initiate infused therapies. Additionally, transportation services can be integrated into the platform to aid with arranging transportation to/from the infusion center if needed to ensure the patient is treated.

For each of these examples, the central platform's network/partners can choose from the above already embedded transactions/microservices and extend to include other transactions/microservices from the services network, such as affordability transactions or adherence programs.

Figure 5:
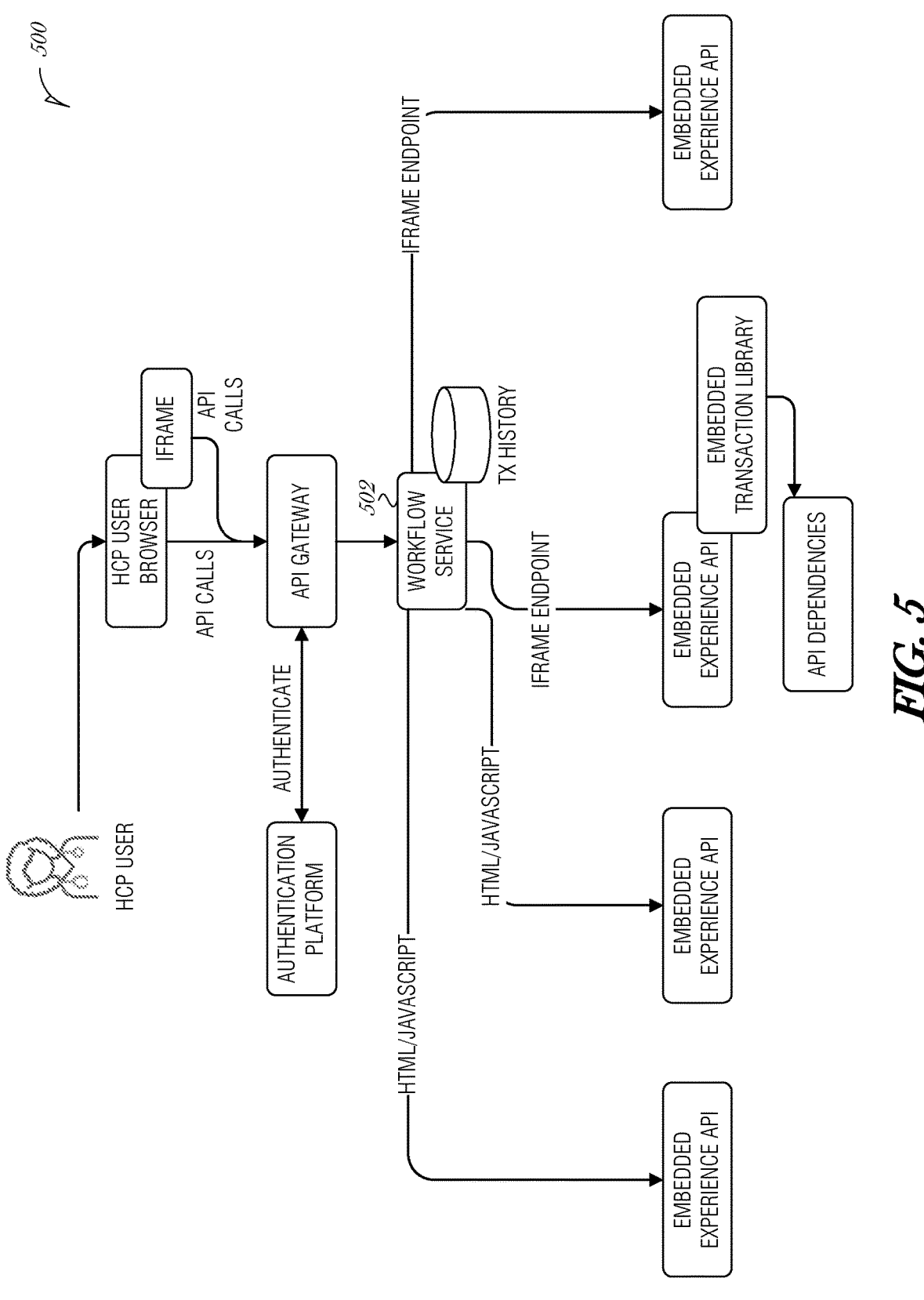
FIG. 5 is another diagram illustrating control and data flow, according to an embodiment.

FIG. 5 is another diagram illustrating control and data flow 500, according to an embodiment. The control and data flow 500 of FIG. 5 demonstrates the modular approach that can be used by partners. A menu of available options may be obtained as described above in FIG. 4. Using parameters that identify the partner, a patient, a treatment or therapy, or the like, various transactions may be initiated to obtain information or initiate a workflow. For instance, to enroll a patient in a therapy for a certain drug, the microservice may be initiated using the command:

POST/API/Access/Patient/
    Workflow?Action=Enroll&Drug={drug}

As another example, to perform benefit verification, the operation may be initiated using the command:

POST/eservices/workflow/invoke/{transactiontype} where transactiontype is one of an enumerated value that may include "medebv" (medical electronic benefit verification). Here, the Body element may include {Patient, ExternalID}. The Patient variable may be identifying information, such as first name, last name, date of birth, social security number, ZIP code, insurance member identifier, payer (e.g., insurance company identification), globally unique identifier, etc. The ExternalID is a unique ID for the partner. The Patient object is used in combination with the ExternalID to uniquely identify the transaction and whether the patient need an enrollment to perform the transaction.

As another example, to check for prior authorization, the operation may be initiated using the command:

POST/API/Access/Patient/
    Workflow?Action=PA&Drug={drug}

A workflow service 502 may be used to check that the requested action is valid given the partner and patient information. Then an appropriate embedded experience API is called to initiate the workflow to obtain information and provide the embedded UI to the HCP user.

The modularity of the system provides HCPs, through network partners, a solution that streamlines the onboarding and management of specialty medications and other therapies, irrespective of the brand of specialty medication offered, and normalizes data for stakeholders in the process.

Figure 6:
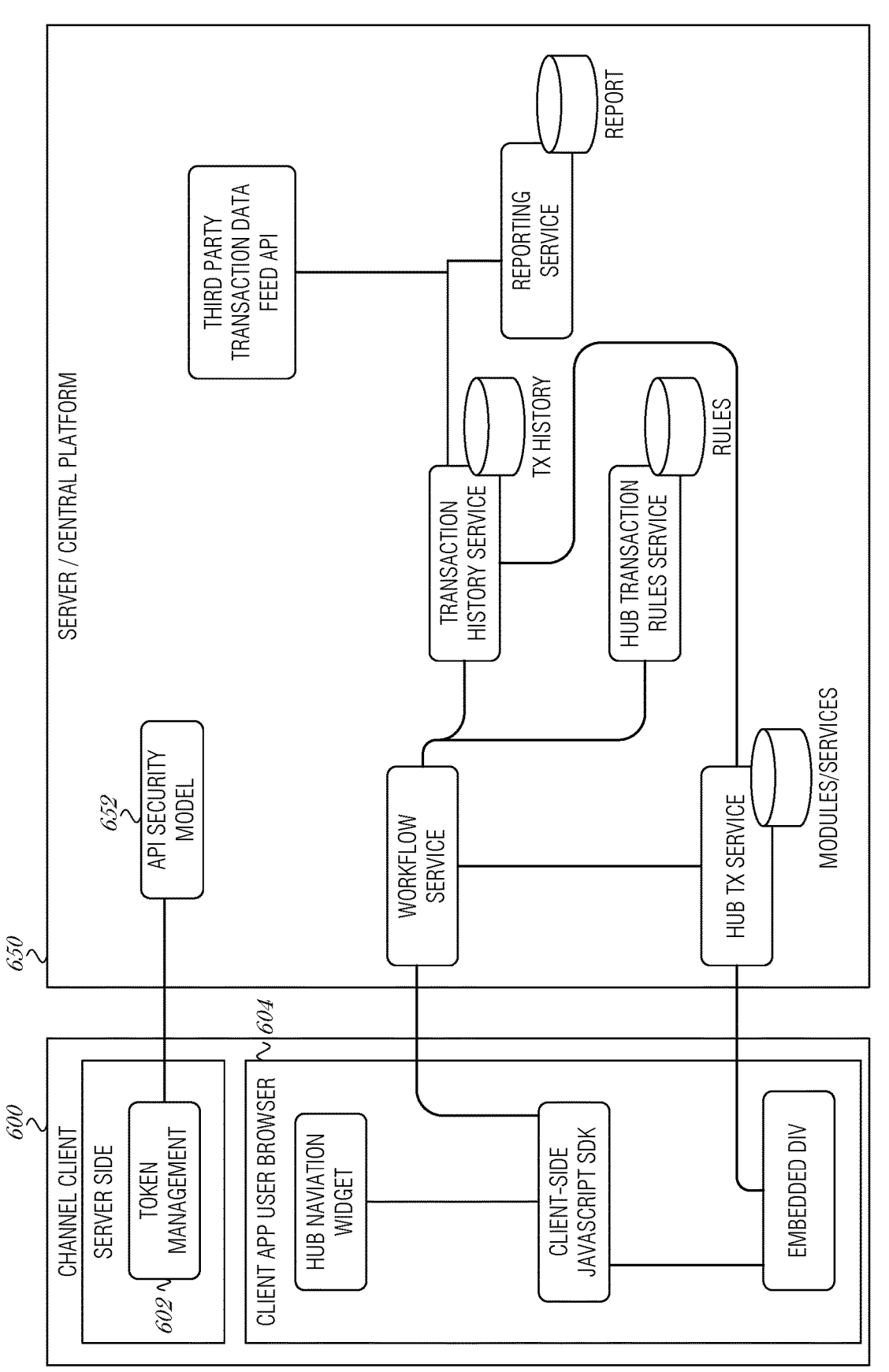
FIG. 6 illustrates control and data flow of components in a client and server, according to an embodiment.

FIG. 6 illustrates control and data flow of components in a client 600 and server 650, according to an embodiment.

The client 600 includes a token manager 602, and a client application 604, which may be a web browser application. The client application 604 is able to render HTML pages with embedded scripting code.

The token manager 602 is used to authenticate with an identity authentication system 652, which may be hosted by the server 650 or may be hosted at a third party system and accessible via an API at the server 650. The token manager 602 may authenticate the client application 604 for a session. The tokens may be implemented with a JSON Web Token (JWT). JWT is an open standard (RFC 7519) that defines a compact and self-contained way for securely transmitting information between parties as a JSON object. This information can be verified and trusted because it is digitally signed. JWTs can be signed using a secret (with the HMAC algorithm) or a public/private key pair using RSA or ECDSA.

Each client gets a token from the authentication process and that is used to uniquely authenticate each partner. Based on the token, the server 650 can validate which drugs and microservices the partner has available to it.

The client application 604 includes an HTML DIV that is rendered with an ID/Class defined by the provider of the central platform. The client application 604 has access to or stores patient context data as a payload. The patient context data may include various aspects, such as the patient identification, practice identification, therapy identification, and transaction type. In response to an event, such as an OnButtonClick( ) event, a transaction is initiated with the server 650. The events may be generated by an operating system (OS) or an operating environment, or the events may be generated by messages passed from the server 650 to the client application 604.

In an example, in response to the OnButtonClick( ) event, the client application 604 gathers patient context and passes the context to an SDK function. The SDK function initiates a microservice workflow with the parameters (payload, JWT, TxType), where the payload is the patient context data, the JWT is a token, and the TxType is the operation or transaction that is selected in the HTML DIV. The SDK populates the client-side DIV with HTML and JavaScript if the transaction is supported. The SDK handles calls to the workflow service and invokes the next action when ready.

Figure 7:
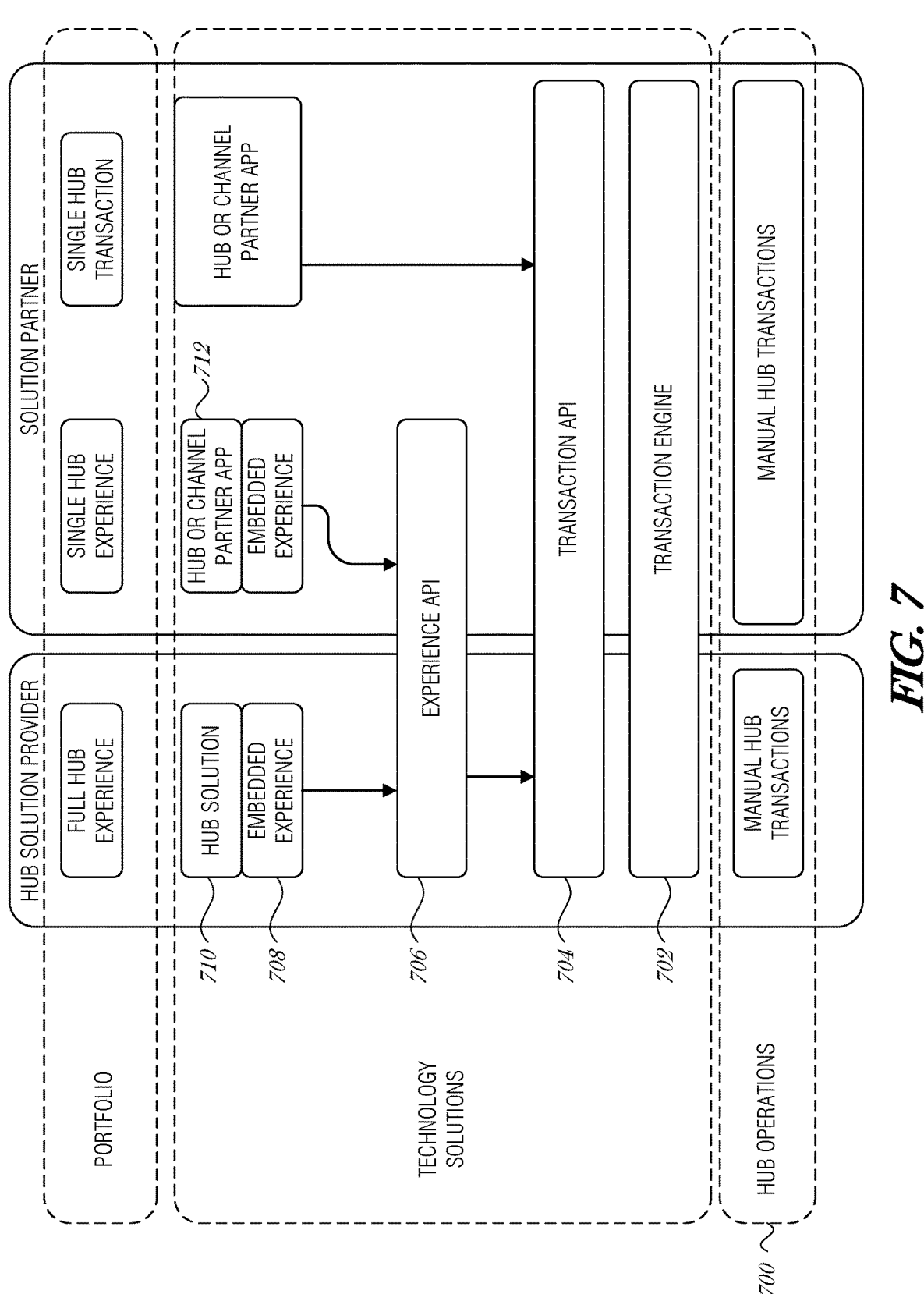
FIG. 7 is a block diagram illustrating high-level components, according to an embodiment.

FIG. 7 is a block diagram illustrating high-level components, according to an embodiment. At the base of architecture are the hub operations 700. Hub operations 700 may be executed for the central platform or for the partners of the central platform. A transaction engine 702 is used to invoke the hub operations 700. A transaction API 704 is used to invoke the services offered by the transaction engine 702. There are two paths to access the transaction API 704, either with an experience API 706 or directly from code. The experience API 706 wraps the transaction API 704 to provide a customized integrated user experience. The experience API 706 is called from an embedded element 708 in an HTML page. The embedded element 708 may be used in a platform solution 710 or a partner solution 712.

The embedded element 708 may be implemented two ways. In a first implementation, the client can consume an embedded experience API 706 in which they will call an API and receive an embeddable JavaScript/HTML payload in response that can be rendered in a client browser application.

In a second implementation, which may be used for enrollment services, an initialization API returns a URL that can be embedded in an IFRAME in the calling client application. The contents of the IFRAME is hosted on the central platform's servers. This is different from the other embedded transaction APIs which return HTML/JavaScript to the calling client to natively embed in the page's document object model.

As illustrated in FIG. 7, the transaction API 704 may be accessed directly. In this situation, the calling client is responsible for all of the user experience and will call APIs that transact data payloads only.

Figure 8:
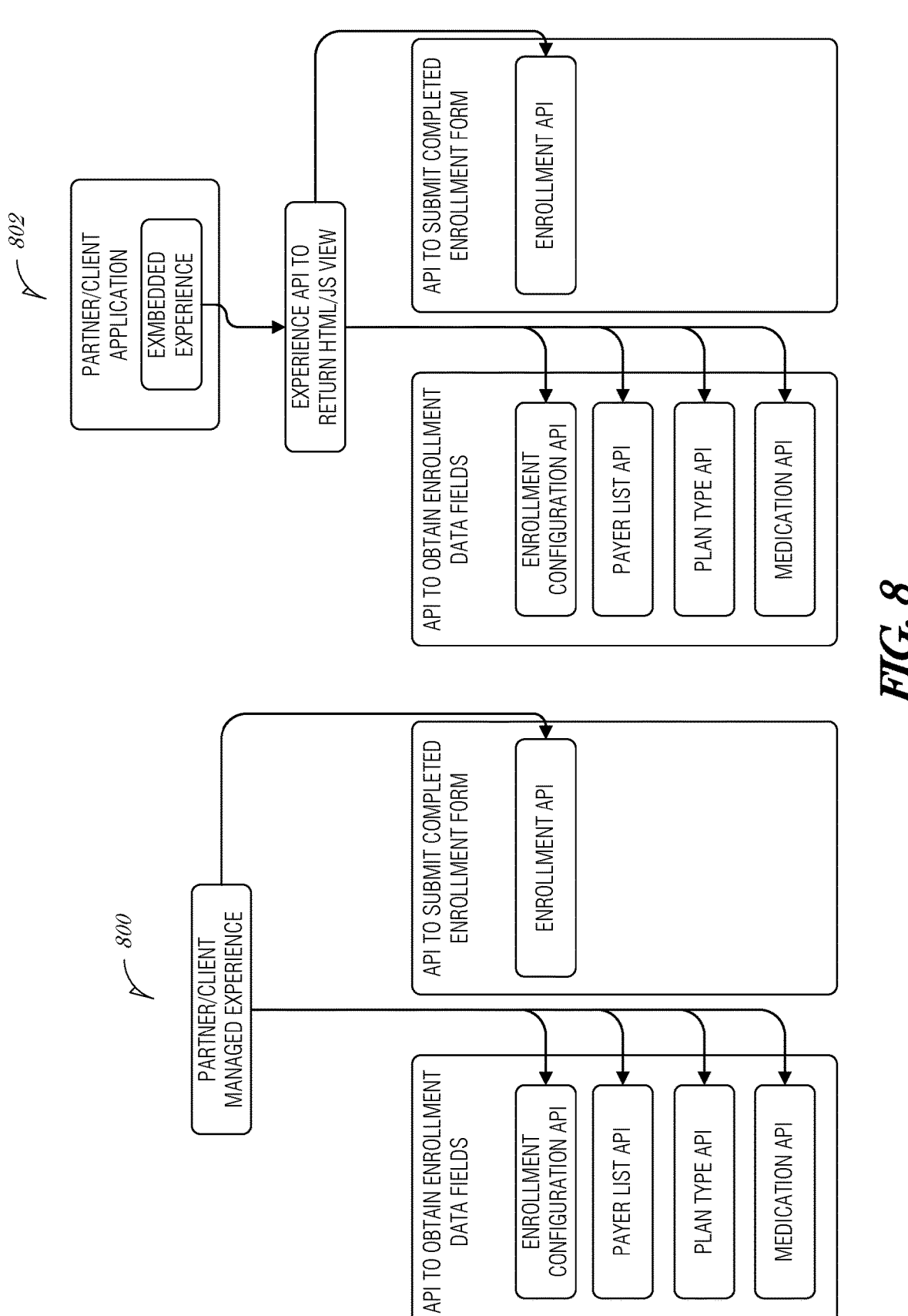
FIG. 8 is another block diagram illustrating high-level components, according to an embodiment.

FIG. 8 is another block diagram illustrating high-level components, according to an embodiment. In a first transaction type 800, the calling client software generates the entire experience and rely on APIs to populate an experience and submit an enrollment data payload.

In a second transaction type 802, the client calls an API that renders a user experience within the calling client. This may be implemented using the embedded experience API 706.

Figure 9:
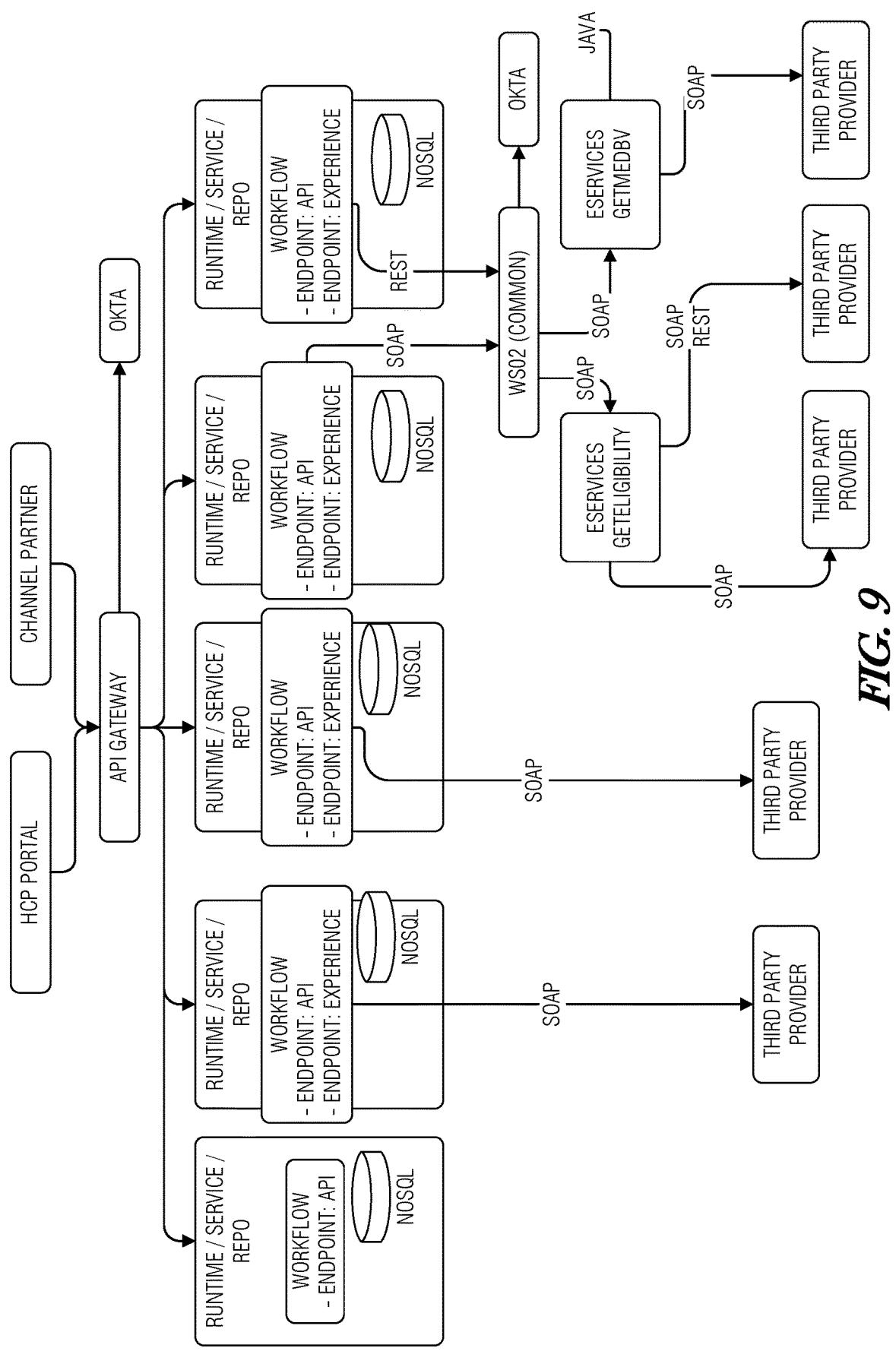
FIG. 9 is another block diagram illustrating high-level components, according to an embodiment.

FIG. 9 is another block diagram illustrating high-level components, according to an embodiment. The central platform creates a microservice runtime for each business domain (e.g., RxBV, MedBV, RxPA, MedPA, enrollment, etc.). Each microservice can support endpoints for headless (i.e., API only) transactions and experience-based transaction APIs (e.g., where the microservice serves HTML snippets back to the calling client).

Each microservice is backed by its own infrastructure that supports rule building, whether manual or with machine learning, to optimize completion of the transaction and trigger the relevant business operations subsequent to transaction completion. The microservices are transaction specific, but are built to handle any drug or other therapy. This enables the central platform to service any drug or therapy using the same set of microservices with specific business rules for each specific drug/therapy.

The central platform consolidates APIs behind a secure application gateway to manage request throttling, have the ability to rehost backend services without impacting client DNS configuration, and manage credentialed access.

The central platform may use gateway and workflow APIs to enable different experience APIs to be chained together in varying order for different clients to support an optimized path to onboard a patient to therapy. The central platform uses a NOSQL solution to flatten data structures with a goal of creating key-based lookups for resources. Database reads and writes are handled through JSON serialization instead of an ORM (Object-Relational Mapping) layer to relational data stores. Microservices do not require dependencies. The object model mirrors the domain model.

Example Use Cases

In a first example use case, a provider prescribes a specialty retina therapy for a patient and needs to know if the patient's health plan will cover the therapy. The provider logs into their core practice software (e.g., EMR, infusion center management software, GPO order management software), selects the patient and therapy, and clicks a 'benefit verification' user interface element. The patient demographic information and insurance information, as well as the provider's practice and credentials, are automatically transferred to an enrollment transaction and a benefit verification (BV) transaction, which then triggers calls to the payer and a BV algorithm to determine coverage, patient out of pocket, prior authorization requirement, buy-and-bill availability, transportation benefits, site of care options, and enrollment to manufacturer sponsored programs. It is a comprehensive BV coordinated across primary, secondary, and tertiary insurances for the specific therapy requested by the provider.

The provider (and patient) are presented with options to enroll in manufacturer sponsored programs, such as copay, educational or adherence programs, and take advantage of payer benefits such as transportation coverage. The provider can see the status of each transaction. For example, the status of a copay, patient assistance program (PAP)/free goods request, or enrollment into an adherence program.

If prior authorization is indicated, the provider can then initiate this process through medical prior authorization (medPA). The patient demographic information, insurance information, and required clinical information, as well as the provider's practice and credentials, can all be automatically transferred to a medical medPA transaction. A process determines the most expedient route of medPA submission to the payer and ensures the required fields are completed. The provider is presented any status returned by the payer, including final determination by the payer. If the payer requirements are satisfied, the provider may then treat the patient. Adherence programs are initiated, including coordination of the transportation benefit.

The workflow is entirely encapsulated between the provider's host/native system of record and the central platform's proprietary transactions/microservices and can be initiated for any therapy the retina specialist prescribes.

In a second example use case, a cardiologist determines that a patient needs an infusion of a specialty therapy but will not be the treating provider (administer the infusion). The cardiologist prescribes the therapy and sends the prescription to the central platform's Non-dispensing Pharmacy (NDP). The NDP receives the prescription and leverages a BV transaction to determine the patient's coverage, including payer approved site of care options (ex/infusion center, ambulatory center, home infusion). The NDP provides site of care options and sponsored program availability to the patient. The cardiologist has visibility into the status via the HCP Portal as the NDP finishes operations to onboard the patient. The NDP submits the medPA via a PA transaction. The NDP identifies a treating provider, coordinates the infusion at the preferred site of care, working with the treating provider and dispensing entity (specialty pharmacy or buy-and-bill scenarios). The NDP obtains treatment confirmation from the treating provider and pushes treatment confirmation back to the referring cardiologist via the HCP portal. The workflow is applicable for any referring physician seeking alternate treatment providers for physician-administered therapies, such as infused or injected therapies.

FIG. 10 is a flowchart illustrating a method 1000 for onboarding patients into an electronic patient management system, according to an embodiment. The method 1000 may be performed by a compute system, or a device, such as compute node 1400 or a computing node 1450.

At 1002, a request for available operations relevant to a patient is received at a workflow service in the electronic patient management system from a client device. The request may include patient identification information of the patient, a healthcare practice identifier, and a therapy identifier. In an embodiment, the request is encapsulated in a microservice application programming interface (API) call.

In an embodiment, the request for available operations includes a security token, the security token obtained during an authentication process conducted by the client device to authenticate to the electronic patient management system.

At 1004, transaction history of the patient is accessed based on the patient identification information.

At 1006, a set of available operations is determined based on the transaction history. In an embodiment, determining the set of available operations based on the transaction history includes accessing a rules database to obtain a set of rules for the patient based on the patient identification information and the therapy identifier, evaluating the set of rules to determine a set of completed transactions and a set of uncompleted transactions, and determining the set of available operations based on the set of uncompleted transactions.

At 1008, the set of available operations is encoded in hypertext code. In an embodiment, the hypertext code is encoded in a JavaScript Object Notation (JSON) data payload. In a related embodiment, the hypertext code includes hypertext markup language (HTML) code. In a related embodiment, the hypertext code includes scripting code.

At 1010, the hypertext code is transmitted to the client device for rendering on a display of the client device.

Figure 11:
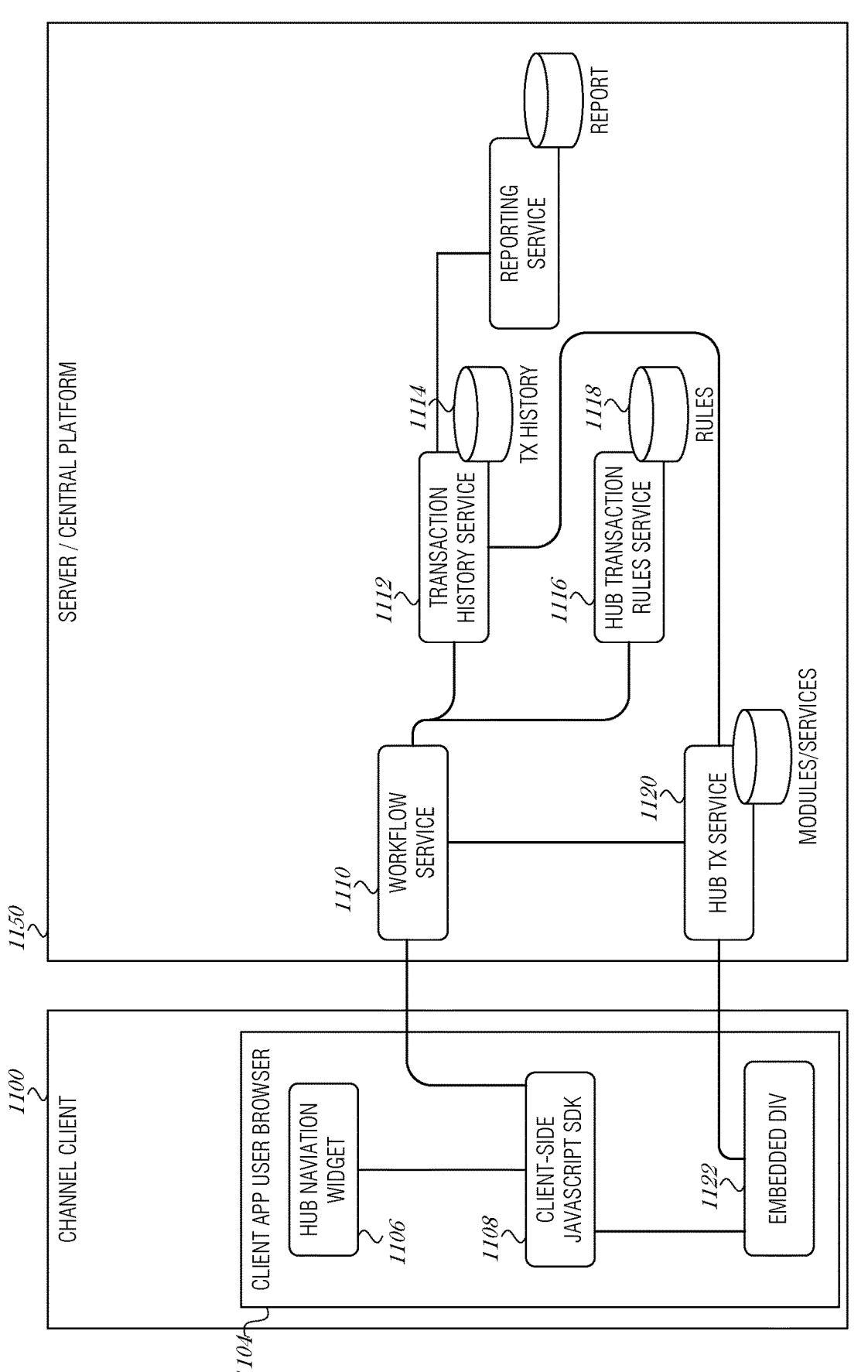
FIG. 11 illustrates control and data flow of components in a client and server, according to an embodiment.

FIG. 11 illustrates control and data flow of components in a client 1100 and server 1150, according to an embodiment. The client may be an instance of the client 600 described in FIG. 6. A client application 1104 executing on the client 1100 provides HTML DIV that is rendered with an ID/Class defined by the provider of the server 1150. The client application 1104 has access to or stores patient context data as a payload. The patient context data may include various aspects, such as the patient identification, practice identification, therapy identification, and transaction type. A transaction is initiated with the server 1150 when a user interface (UI) event occurs, such as when a user activates a button, clicks a link, or the like. In an example, in response to the UI event, the client application 1104 gathers patient context (e.g., reads from a file or a database accessible to the client application 1104) and passes the context to an SDK function as a parameter. The SDK function initiates a microservice workflow with the parameters (payload, JWT, TxType), where the payload is the patient context data, the JWT is a security token, and the TxType is the operation or transaction that is selected by the user in the UI of the HTML DIV. The SDK will populate the client-side DIV with HTML and JavaScript if the transaction is supported. The SDK handles calls to the workflow service 1110 and invokes the next action when ready.

In the example illustrated in FIG. 11, a hub navigation widget 1106 is used to display options to the user in a UI. The options may be presented in various UI controls, such as a drop down list, a hyperlink, a control button, or the like. Upon activation of the UI control in the hub navigation widget 1106, the client-side SDK 1108 is invoked. For instance, the user may want to check whether a patient has prior authorization for a drug treatment. As such, in an example, the user may select a patient (e.g., select a patient name from a drop down list), and click a button to perform a medical prior authorization (PA) or benefit verification (BV) check. The client-side SDK 1108 invokes a service call to the workflow service 1110. The workflow service 1110 may include one or more exposed microservices built using an application programming interface (API), such as a RESTful API.

Based on the transaction type (TxType), the workflow service 1110 may perform various operations. For instance, continuing with the example from above, if the transaction type is a PA check, then the workflow service 1110 may first invoke the transaction history service 1112 to query a transaction log 1114 and obtain transaction history for the patient involved. The workflow service 1110 may also perform other data gathering operations to obtain the data needed to initiate a medPA check with a payer. The medPA process is used to determine whether the drug therapy ordered by the HCP is approved by the payer (e.g., insurance company) prior to the patient being treated.

To contact the payer, there may be several communication pathways available. For instance, a payer may provide a telephonic communication pathway to contact a human operator or access an automated phone system. The payer may also provide other communication pathways, such as a secure email service, a text messaging service, a business-to-business connection, an application programming interface (API) exposed by the payer to the platform, or a facsimile channel.

The workflow service 1110 may implement a machine learning technique to determine a preferred communication pathway for a patient with the unique patient context of that patient. The workflow service 1110 may interface with the hub transaction rules service 1116 to provide the hub transaction rules service 1116 patient data and then obtain the preferred communication pathway.

The hub transaction rules service 1116 (also referred to as a rules engine), may be used to select the communication pathway. The hub transaction rules service 1116 may query a rules database 1118. The rules database 1118 may be configured by an administrator of the central system based on various policies received from drug manufacturers, health care providers, health care insurers, or the like. The hub transaction rules service 1116 may be implement rules that are determined based on a machine learning technique.

In an example, a rules-based technique is used independent of or with a machine learning technique to determine a preferred communication pathway. For instance, the rules may be arbitrary, set based on past experience of an administrator, or driven by business policies. The rules may be used in a weighted function. Alternatively, the rules-based technique may make use of or be implemented with supervised machine learning, such as with a decision tree. The rules-based technique may use patient data inputs, such as those described above. Based on determinative probability analysis, a rules-based technique may weight various inputs and then make decisions based on their values compared to historical values of similar patients.

In an example, a model may be trained using supervised machine learning based on a number of features. The features may include a time from medPA submission to decision, an amount of data required for the medPA submission, a follow up frequency, a denial rate, an approval rate, an approved as requested rate, a preferred user experience score, a payer discrete response type, a recency factor, and the like. A medPA request to final decision or disposition may be regarded as a transaction. The medPA transaction may have one or more features that are used to model the transaction. A number of transactions are included in the model so that the model is able to account for the effects of each feature in view of the result—a successful medPA disposition.

The features include the time from medPA submission (e.g., request) to decision (e.g., final disposition), which may be measured in days, hours, or other units of time. The amount of data required for the medPA submission may be measured in number of data items (e.g., name, address, patient identifier, and so on), the number of forms, or other measures of data. The follow up frequency is a measure of the number of times necessary to interact with a payer to get final disposition (e.g., approval/denial) in a medPA transaction. The denial rate is an overall measure of how many medPA requests are denied. The denial rate may be filtered for denials for a certain patient population, a certain drug or therapy, a certain medical practice, a certain payer, or the like. The approval rate is an overall measure of how many medPA requests are approved in whole or in part. Like the denial rate, the approval rate may be filtered for approvals for a certain patient population, a certain drug or therapy, a certain medical practice, a certain payer, or the like. The approved as requested rate is an overall measure of how many medPA requests are approved in whole as requested by the prescribing physician. Like the denial and approval rates, the approved as requested rate may be filtered for approvals for a certain patient population, a certain drug or therapy, a certain medical practice, a certain payer, or the like. The preferred user experience score is a value provided by a patient reflecting their experience during the prior authorization process. The preferred user experience score may be scaled between two numerical values (e.g., 1-10, 1-5, etc.), be a letter grade (e.g., A, B, C, etc.), or be provided in other terms. The payer discrete response type indicates whether a payer's response to a medPA request used the same communication pathway as the request. For instance, if the request was submitted over the phone but the response is by fax, then the response pathway type is discrete (or different) from the request pathway. The recency factor may be used to weight more recent transactions more than older transactions. This may be a reflection that recent transactional data is more valuable or relevant than older transactional data.

The model may assign a relative weighting to some or all of the features in order to weight some of the features higher or lower than other features. For example, more recent transactions may be weighted higher than older transactions. As another example, the time from submission to decision may have a higher weight than the payer discrete response type. The model may be used to determine a communication pathway that provides the optimal chance of obtaining a successful response to a prior authentication request. The model may also be used to sort available communication pathways according to their respective likelihood of obtaining a final disposition of a prior authentication request (e.g., approval or denial).

Based on the evaluation of the rules, the hub transaction rules service 1116 may select a communication pathway where the selection represents the optimal pathway, and inform the workflow service 1110 of the result. The workflow service 1110 may then initiate various communications with a payer, patient, or health care provider, based on how the workflow service 1110 is configured for the selected communication pathway.

The workflow service 1110 may then initiate communication with the payer to obtain the medPA. Depending on the type of communication pathway selected, this may include actions such as formatting the medPA request to conform to the payer's configuration, encrypting or securing the request, encoding the request for the payer, establishing a communication channel (e.g., a telephone call, a business-to-business link, a database connection, use of an application programming interface, etc.), and then transmitting the medPA request to the payer for evaluation. As responses are received from the payer for respective medPA requests, the responses may be used as a feedback mechanism to the ML model in order to modify later executions of the model.

The workflow service 1110, or another part of the server 1150, receives the response regarding the medPA request from the payer. The response may be provided in a format defined by the server 1150 to enable consistent data accuracy. This also may make data ingestion easier for the hub transactions service 1120 or other part of the server 1150 for logging, reporting, or other data transformations.

The hub transactions service 1120 may, in response to a medical electronic prior authorization query for a patient, produce renderable HTML code and return the code to be rendered in an embedded DIV element 1122 in the client's user browser 1104. For instance, a JavaScript/HTML payload may be transmitted to the embedded DIV element 1122, which can be rendered in the client browser application 1104. The renderable code may show the result of the medPA from the payer.

Alternatively, in another example, a URL is returned that can be embedded in an IFRAME in the calling client application. The contents of the IFRAME is hosted by the central platform 1150. This is different from the other embedded transaction APIs that return HTML/JavaScript to the calling client to natively embed in the page's document object model. The user of the client browser application 1104 can seamlessly interact with the user experience in the IFRAME to enroll the patient.

Figure 12:
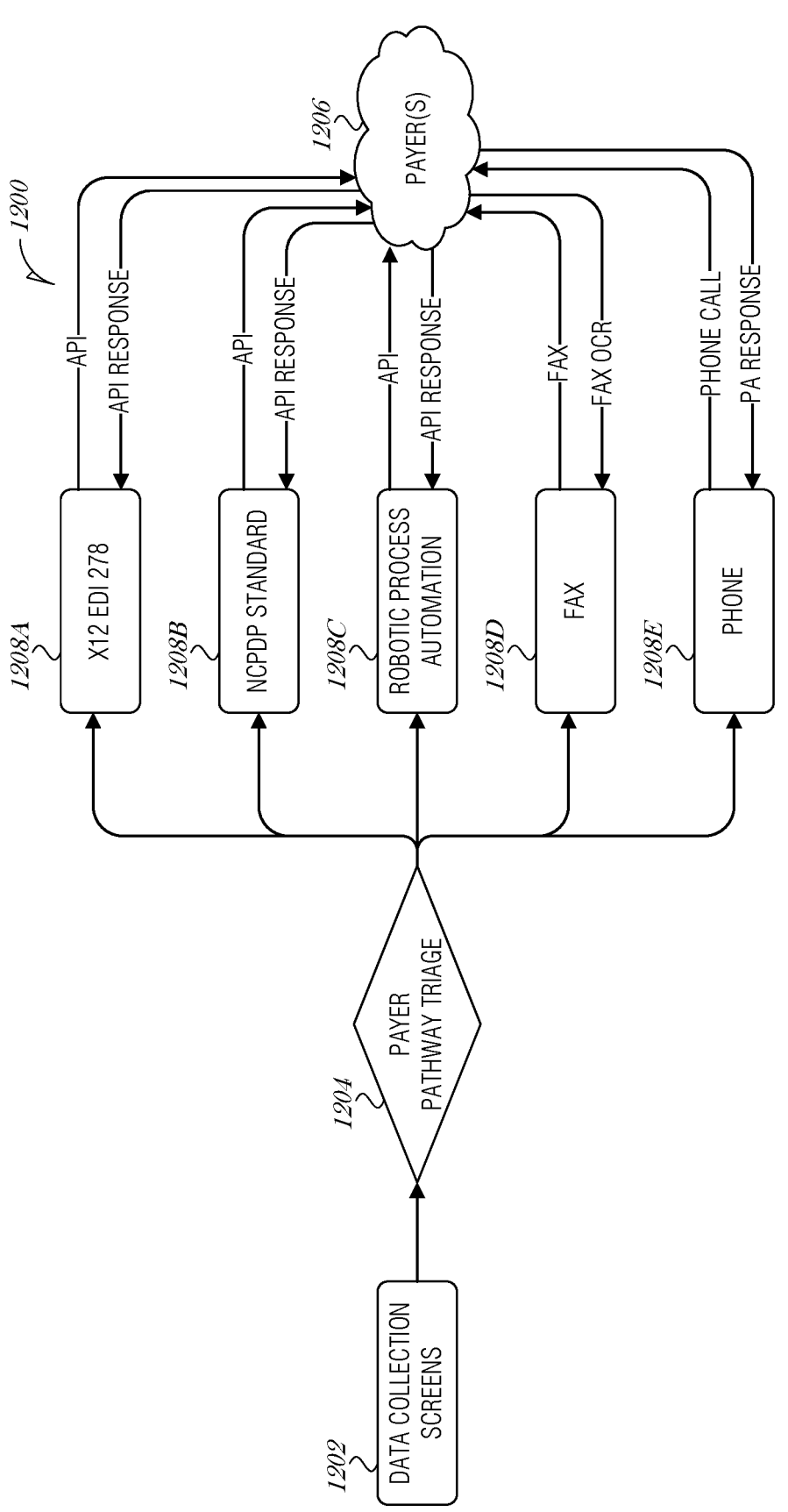
FIG. 12 is a block diagram illustrating data and control flow in a payer pathway triage process, according to an embodiment.

FIG. 12 is a block diagram illustrating data and control flow in a payer pathway triage process 1200, according to an embodiment. The process 1200 may be performed by a compute system, a device, such as compute node 1400, a computing node 1450, a system 1150, or one or more servers in a server system in an electronic patient management system.

A set of data collection screens 1202 are used to collect patient data, practice data, treatment data, insurance data, and other data needed to perform a medical prior authorization (medPA). The data is transmitted to an electronic patient management system, such as the central platform 202.

The communication pathways include an ANSI X12 EDI 278 transaction set communication pathway 1208A, a National Council for Prescription Drug Programs (NCPDP) communication standard pathway 1208B, a robotic process automation (RPA) communication pathway 1208C, a facsimile communication pathway 1208D, and a telephone communication pathway 1208E. Another communication pathway may a message formatted in accordance with the HL7® Fast Health Interoperability Resources (FHIR®)-based drug reference specification. It is understood that pathways may be added or removed and that the pathways described here are for illustration and are non-limiting.

A payer pathway triage decision system 1204 is used to determine which communication pathways 1208A-E are available for a payer 1206 or a set of payers, and then sort the available communication pathways 1208A-E into an order from a most-likely to lead to a successful prior authorization to a least-likely to lead to a successful prior authorization. Communication using the communication pathways 1208A-E may then be initiated in the sorted order and if one fails, then the next in the order may be used. Failure may be due to technical difficulties (e.g., a web service is down or an IP address is unreachable) or may be due to other reasons (e.g., a website address is misspelled). Failure may also be detected by an automated email reply (e.g., bounced email), a lack of response (e.g., connection timeout), no confirmatory response after a timeout period, a system access failure, etc. In some cases, failure is detected nearly immediately, such as when a database or service is unavailable. In other cases, failure is detected after a timeout period. The timeout period may be configurable. For instance, if after a medPA request is submitted, a confirmatory message is not received in an allotted time (e.g., 10 minutes), then the medPA request is assumed to have been lost or ignored. In this case, the communication pathway used to submit the medPA request is considered failed, and a new communication pathway may be used.

Figure 13:
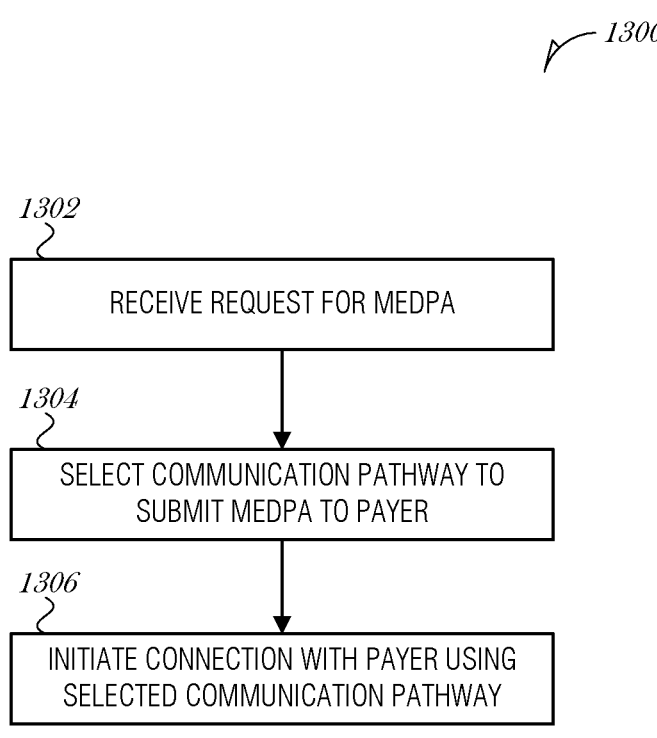
FIG. 13 is a flowchart illustrating a method for managing communication, according to an embodiment.

FIG. 13 is a flowchart illustrating a method 1300 for managing communication, according to an embodiment. The method 1300 may be performed by a server system, a device, such as compute node 1400, a computing node 1450, a system 1150, or one or more compute nodes in a server system of an electronic patient management system.

At 1302, an electronic request to obtain a medical prior authorization (medPA) for a specialty drug to administer for a patient of the healthcare practice is received from a user at a healthcare practice. The user may be an administrative assistance, a physician's assistant, a prescribing physician, or other person who is seeking a medPA for a patient.

In an embodiment, the electronic request to obtain the medPA is encoded in a Hypertext Transfer Protocol (HTTP) message request for prior authorization of a patient treatment. In another embodiment, the Hypertext Transfer Protocol (HTTP) message request is an eXtended Markup Language (XML) Simple Object Access Protocol (SOAP) message. In a related embodiment, the Hypertext Transfer Protocol (HTTP) message request is a Representational State Transfer (REST) message.

In an embodiment, the electronic request to obtain the medPA includes patient context data. In a further embodiment, the patient context data is received from a drug prescriber. In another embodiment, the patient context data is obtained from a partner system.

At 1304, a communication pathway to submit the medPA to a healthcare payer is selected from a plurality of communication pathways. The selection may be performed by a rules service executing at the server system.

In an embodiment, the rules service is configured using machine learning. In an embodiment, the rules service is configured to using a weighted function to select the communication pathway. In a further embodiment, the weighted function includes a recency weight. For instance, recent transactions may be assigned a higher weight on the pathway selection process compared to older transactions.

In an embodiment, the rules service is configured to use a weighted function to sort the plurality of communication pathways. In a further embodiment, the weighted function includes a recency weight.

In an embodiment, the rules service is configured to select the communication pathway using a plurality of factors. In a further embodiment, the plurality of factors may include one or more of: a time from medPA submission to decision, an amount of data required for the medPA submission, a follow up frequency, a denial rate, an approval rate, an approved as requested rate, a preferred user experience score, a payer discrete response type, or a recency factor.

In an embodiment, the rules service is configured to sort the plurality of communication pathways using a plurality of factors. In a further embodiment, the plurality of factors include one or more of: a time from medPA submission to decision, an amount of data required for the medPA submission, a follow up frequency, a denial rate, an approval rate, an approved as requested rate, a preferred user experience score, a payer discrete response type, or a recency factor.

In another embodiment, the rules service is configured to sort the plurality of communication pathways in order of a most likely to obtain a timely response to a least likely to obtain a timely response. The period to measure whether a response is timely is based on user expectations and industry standard. In some cases, a response in twenty-four hours may be considered timely, whereas in other cases a response in 30 seconds may be considered timely. Timeliness of a response may also be a function of or be based on the type of communication pathway used. For instance, a timely response for a request submitted electronically through an API to a payer portal may be three minutes, whereas a timely response for a request submitted by post mail may be three weeks.

In a further embodiment, initiating the connection with the healthcare payer using the selected communication pathway includes iteratively initiating connections with the healthcare payer to obtain the medPA using the sorted plurality of communication pathways. In a further embodiment, iteratively initiating connections with the healthcare payer comprises attempting a first connection using a first communication pathway of the sorted plurality of communication pathways and attempting a second connection using a second communication pathway of the sorted plurality of communication pathways, when the first connection fails, wherein the second communication pathway is ranked lower than the first communication pathway in the sorted plurality of communication pathways.

In embodiments, the plurality of communication pathways include: a business-to-business connection, an application programming interface exposed by the healthcare payer to the server system, a facsimile channel, or a telephone representative.

In embodiments, the plurality of communication pathways include at least two of: an ANSI X12 EDI 278 transaction set pathway, a National Council for Prescription Drug Programs (NCPDP) communication standard pathway, a robotic process automation (RPA) communication pathway, a facsimile communication pathway, a telephone communication pathway, or a HL7 FHIR-based drug format pathway.

At 1306, a connection with the healthcare payer is initiated using the selected communication pathway. Initiating the connection may include transmitting an email message, initiating a phone call, accessing an API, or performing a direct business-to-business function over a dedicated connection, for example. Further, depending on the type of communication pathway selected, this may include actions such as formatting the medPA request to conform to the payer's configuration, encrypting or securing the request, encoding the request for the payer, establishing a communication channel, and then transmitting the medPA request to the payer for evaluation.

In an embodiment, the medPA is included in a medical benefit verification (medBV) for the specialty drug, and the method 1300 includes determining whether the medPA is required as a portion of the medBV using machine learning. An ML capability is used to infer which response will be optimal, based on past experience, as defined by the identified parameters.

Example Architectures

In further examples, any of the compute nodes or devices discussed with reference to the present computing systems and environment may be fulfilled based on the components depicted in FIGS. 14A and 14B. Respective compute nodes may be embodied as a type of device, appliance, computer, or other "thing" capable of communicating with other devices, networking, or endpoint components. For example, a compute device may be embodied as a personal computer, server, smartphone, a mobile compute device, a smart appliance, an in-vehicle compute system (e.g., a navigation system), a self-contained device having an outer case, shell, etc., or other device or system capable of performing the described functions.

Figure 14A:
FIG. 14A provides an overview of example components for compute deployed at a compute node in a computing system.

In the simplified example depicted in FIG. 14A, a compute node 1400 includes a compute engine (also referred to herein as "compute circuitry") 1402, an input/output (I/O) subsystem (also referred to herein as "I/O circuitry") 1408, data storage (also referred to herein as "data storage circuitry") 1410, a communication circuitry subsystem 1412, and, optionally, one or more peripheral devices (also referred to herein as "peripheral device circuitry") 1414. In other examples, respective compute devices may include other or additional components, such as those typically found in a computer (e.g., a display, peripheral devices, etc.). Additionally, in some examples, one or more of the illustrative components may be incorporated in, or otherwise form a portion of, another component.

The compute node 1400 may be embodied as any type of engine, device, or collection of devices capable of performing various compute functions. In some examples, the compute node 1400 may be embodied as a single device such as an integrated circuit, an embedded system, a field-programmable gate array (FPGA), a system-on-a-chip (SOC), or other integrated system or device. In the illustrative example, the compute node 1400 includes or is embodied as a processor (also referred to herein as "processor circuitry") 1404 and a memory (also referred to herein as "memory circuitry") 1406. The processor 1404 may be embodied as any type of processor(s) capable of performing the functions described herein (e.g., executing an application). For example, the processor 1404 may be embodied as a multi-core processor(s), a microcontroller, a processing unit, a specialized or special purpose processing unit, or other processor or processing/controlling circuit.

In some examples, the processor 1404 may be embodied as, include, or be coupled to an FPGA, an application specific integrated circuit (ASIC), reconfigurable hardware or hardware circuitry, or other specialized hardware to facilitate performance of the functions described herein. Also in some examples, the processor 1404 may be embodied as a specialized x-processing unit (xPU) also known as a data processing unit (DPU), infrastructure processing unit (IPU), or network processing unit (NPU). Such an xPU may be embodied as a standalone circuit or circuit package, integrated within an SOC, or integrated with networking circuitry (e.g., in a SmartNIC, or enhanced SmartNIC), acceleration circuitry, storage devices, storage disks, or AI hardware (e.g., GPUs or programmed FPGAs). Such an xPU may be designed to receive, retrieve and/or otherwise obtain programming to process one or more data streams and perform specific tasks and actions for the data streams (such as hosting microservices, performing service management or orchestration, organizing or managing server or data center hardware, managing service meshes, or collecting and distributing telemetry), outside of the CPU or general purpose processing hardware. However, it will be understood that a xPU, a SOC, a CPU, and other variations of the processor 1404 may work in coordination with each other to execute many types of operations and instructions within and on behalf of the compute node 1400.

The memory 1406 may be embodied as any type of volatile (e.g., dynamic random access memory (DRAM), etc.) or non-volatile memory or data storage capable of performing the functions described herein. Volatile memory may be a storage medium that requires power to maintain the state of data stored by the medium. Non-limiting examples of volatile memory may include various types of random access memory (RAM), such as DRAM or static random access memory (SRAM). One particular type of DRAM that may be used in a memory module is synchronous dynamic random access memory (SDRAM).

In an example, the memory device (e.g., memory circuitry) is any number of block addressable memory devices, such as those based on NAND or NOR technologies (for example, Single-Level Cell ("SLC"), Multi-Level Cell ("MLC"), Quad-Level Cell ("QLC"), Tri-Level Cell ("TLC"), or some other NAND). In some examples, the memory device(s) includes a byte-addressable write-in-place three dimensional crosspoint memory device, or other byte addressable write-in-place non-volatile memory (NVM) devices, such as single or multi-level Phase Change Memory (PCM) or phase change memory with a switch (PCMS), NVM devices that use chalcogenide phase change material (for example, chalcogenide glass), resistive memory including metal oxide base, oxygen vacancy base and Conductive Bridge Random Access Memory (CB-RAM), nanowire memory, ferroelectric transistor random access memory (FeTRAM), magneto resistive random access memory (MRAM) that incorporates memristor technology, spin transfer torque (STT)-MRAM, a spintronic magnetic junction memory based device, a magnetic tunneling junction (MTJ) based device, a DW (Domain Wall) and SOT (Spin Orbit Transfer) based device, a thyristor based memory device, a combination of any of the above, or other suitable memory. A memory device may also include a three-dimensional crosspoint memory device (e.g., Intel® 3D XPoint™ memory), or other byte addressable write-in-place nonvolatile memory devices. The memory device may refer to the die itself and/or to a packaged memory product. In some examples, 3D crosspoint memory (e.g., Intel® 3D XPoint™ memory) may include a transistor-less stackable cross point architecture in which memory cells sit at the intersection of word lines and bit lines and are individually addressable and in which bit storage is based on a change in bulk resistance. In some examples, all or a portion of the memory 1406 may be integrated into the processor 1404. The memory 1406 may store various software and data used during operation such as one or more applications, data operated on by the application(s), libraries, and drivers.

In some examples, resistor-based and/or transistor-less memory architectures include nanometer scale phase-change memory (PCM) devices in which a volume of phase-change material resides between at least two electrodes. Portions of the example phase-change material exhibit varying degrees of crystalline phases and amorphous phases, in which varying degrees of resistance between the at least two electrodes can be measured. In some examples, the phase-change material is a chalcogenide-based glass material. Such resistive memory devices are sometimes referred to as memristive devices that remember the history of the current that previously flowed through them. Stored data is retrieved from example PCM devices by measuring the electrical resistance, in which the crystalline phases exhibit a relatively lower resistance value(s) (e.g., logical "0") when compared to the amorphous phases having a relatively higher resistance value(s) (e.g., logical "1").

Example PCM devices store data for long periods of time (e.g., approximately 10 years at room temperature). Write operations to example PCM devices (e.g., set to logical "0", set to logical "1", set to an intermediary resistance value) are accomplished by applying one or more current pulses to the at least two electrodes, in which the pulses have a particular current magnitude and duration. For instance, a long low current pulse (SET) applied to the at least two electrodes causes the example PCM device to reside in a low-resistance crystalline state, while a comparatively short high current pulse (RESET) applied to the at least two electrodes causes the example PCM device to reside in a high-resistance amorphous state.

In some examples, implementation of PCM devices facilitates non-von Neumann computing architectures that enable in-memory computing capabilities. Generally speaking, traditional computing architectures include a central processing unit (CPU) communicatively connected to one or more memory devices via a bus. As such, a finite amount of energy and time is consumed to transfer data between the CPU and memory, which is a known bottleneck of von Neumann computing architectures. However, PCM devices minimize and, in some cases, eliminate data transfers between the CPU and memory by performing some computing operations in-memory. Stated differently, PCM devices both store information and execute computational tasks. Such non-von Neumann computing architectures may implement vectors having a relatively high dimensionality to facilitate hyperdimensional computing, such as vectors having 10,000 bits. Relatively large bit width vectors enable computing paradigms modeled after the human brain, which also processes information analogous to wide bit vectors.

The compute circuitry 1402 is communicatively coupled to other components of the compute node 1400 via the I/O subsystem 1408, which may be embodied as circuitry and/or components to facilitate input/output operations with the compute circuitry 1402 (e.g., with the processor 1404 and/or the main memory 1406) and other components of the compute circuitry 1402. For example, the I/O subsystem 1408 may be embodied as, or otherwise include, memory controller hubs, input/output control hubs, integrated sensor hubs, firmware devices, communication links (e.g., point-to-point links, bus links, wires, cables, light guides, printed circuit board traces, etc.), and/or other components and subsystems to facilitate the input/output operations. In some examples, the I/O subsystem 1408 may form a portion of a system-on-a-chip (SoC) and be incorporated, along with one or more of the processor 1404, the memory 1406, and other components of the compute circuitry 1402, into the compute circuitry 1402.

The one or more illustrative data storage devices/disks 1410 may be embodied as one or more of any type(s) of physical device(s) configured for short-term or long-term storage of data such as, for example, memory devices, memory, circuitry, memory cards, flash memory, hard disk drives, solid-state drives (SSDs), and/or other data storage devices/disks. Individual data storage devices/disks 1410 may include a system partition that stores data and firmware code for the data storage device/disk 1410. Individual data storage devices/disks 1410 may also include one or more operating system partitions that store data files and executables for operating systems depending on, for example, the type of compute node 1400.

The communication circuitry 1412 may be embodied as any communication circuit, device, or collection thereof, capable of enabling communications over a network between the compute circuitry 1402 and another compute device (e.g., a gateway of an implementing computing system). The communication circuitry 1412 may be configured to use any one or more communication technology (e.g., wired or wireless communications) and associated protocols (e.g., a cellular networking protocol such a 3GPP 4G or 5G standard, a wireless local area network protocol such as IEEE 802.11/Wi-Fi®, a wireless wide area network protocol, Ethernet, Bluetooth®, Bluetooth Low Energy, a IoT protocol such as IEEE 802.15.4 or ZigBee®, low-power wide-area network (LPWAN) or low-power wide-area (LPWA) protocols, etc.) to effect such communication.

The illustrative communication circuitry 1412 includes a network interface controller (NIC) 1420, which may also be referred to as a host fabric interface (HFI). The NIC 1420 may be embodied as one or more add-in-boards, daughter cards, network interface cards, controller chips, chipsets, or other devices that may be used by the compute node 1400 to connect with another compute device (e.g., a gateway node). In some examples, the NIC 1420 may be embodied as part of a system-on-a-chip (SoC) that includes one or more processors, or included on a multichip package that also contains one or more processors. In some examples, the NIC 1420 may include a local processor (not shown) and/or a local memory (not shown) that are both local to the NIC 1420. In such examples, the local processor of the NIC 1420 may be capable of performing one or more of the functions of the compute circuitry 1402 described herein. Additionally, or alternatively, in such examples, the local memory of the NIC 1420 may be integrated into one or more components of the client compute node at the board level, socket level, chip level, and/or other levels.

Additionally, in some examples, a respective compute node 1400 may include one or more peripheral devices 1414. Such peripheral devices 1414 may include any type of peripheral device found in a compute device or server such as audio input devices, a display, other input/output devices, interface devices, and/or other peripheral devices, depending on the particular type of the compute node 1400. In further examples, the compute node 1400 may be embodied by a respective compute node (whether a client, gateway, or aggregation node) in a computing system or like forms of appliances, computers, subsystems, circuitry, or other components.

Figure 14B:
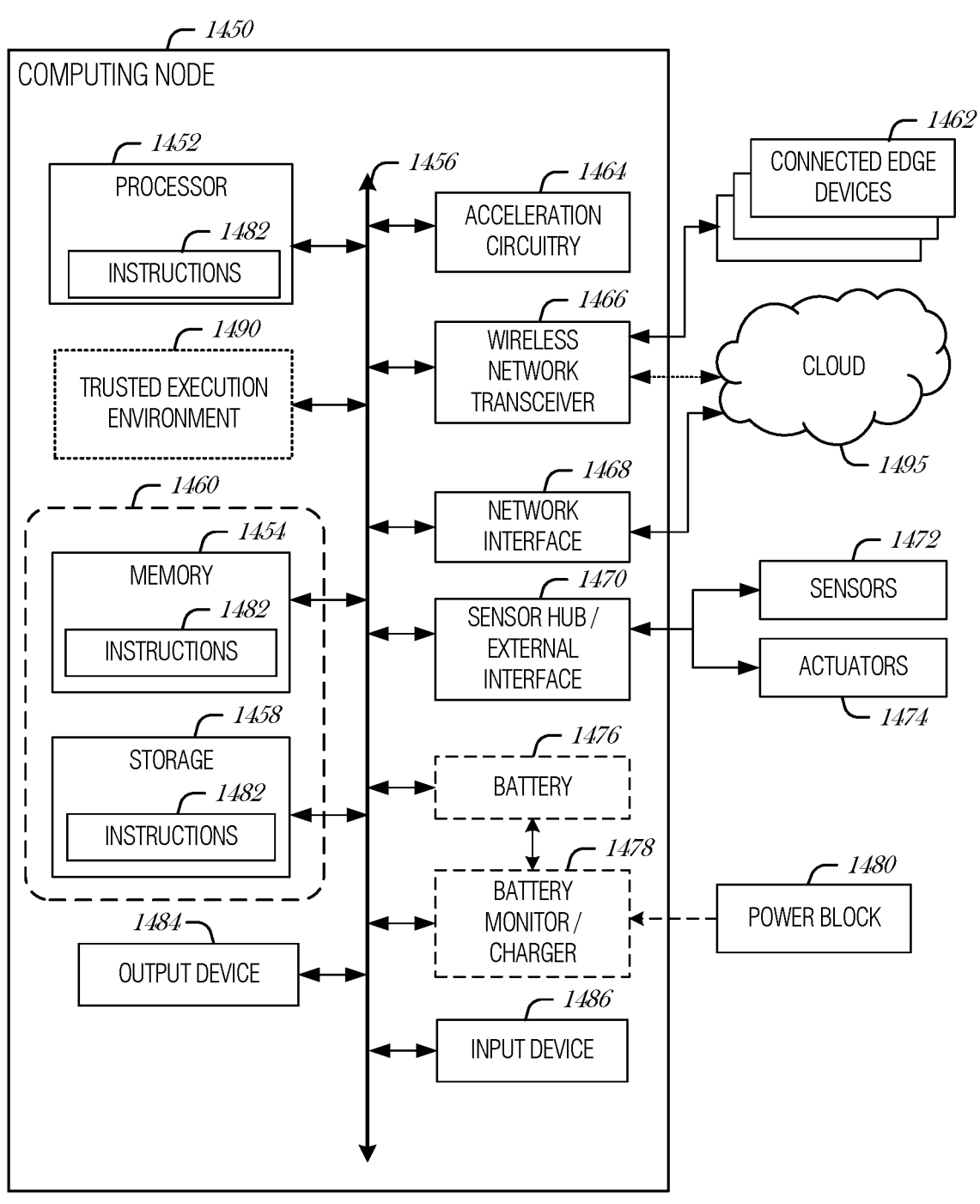
FIG. 14B provides a further overview of example components within a computing device in a computing system.

In a more detailed example, FIG. 14B illustrates a block diagram of an example of components that may be present in a computing node 1450 for implementing the techniques (e.g., operations, processes, methods, and methodologies) described herein. This computing node 1450 provides a closer view of the respective components of node 1400 when implemented as or as part of a computing device (e.g., as a mobile device, a base station, server, gateway, etc.). The computing node 1450 may include any combination of the hardware or logical components referenced herein, and it may include or couple with any device usable with a communication network or a combination of such networks. The components may be implemented as integrated circuits (ICs), portions thereof, discrete electronic devices, or other modules, instruction sets, programmable logic or algorithms, hardware, hardware accelerators, software, firmware, or a combination thereof adapted in the computing node 1450, or as components otherwise incorporated within a chassis of a larger system.

The computing device 1450 may include processing circuitry in the form of a processor 1452, which may be a microprocessor, a multi-core processor, a multithreaded processor, an ultra-low voltage processor, an embedded processor, an xPU/DPU/IPU/NPU, special purpose processing unit, specialized processing unit, or other known processing elements. The processor 1452 may be a part of a system on a chip (SoC) in which the processor 1452 and other components are formed into a single integrated circuit, or a single package, such as the Edison™ or Galileo™ SoC boards from Intel Corporation, Santa Clara, California. As an example, the processor 1452 may include an Intel® Architecture Core™ based CPU processor, such as a Quark™, an Atom™, an i3, an i5, an i7, an i9, or an MCU-class processor, or another such processor available from Intel®. However, any number other processors may be used, such as available from Advanced Micro Devices, Inc. (AMD®) of Sunnyvale, California, a MIPS®-based design from MIPS Technologies, Inc. of Sunnyvale, California, an ARM®-based design licensed from ARM Holdings, Ltd. or a customer thereof, or their licensees or adopters. The processors may include units such as an A5-A13 processor from Apple® Inc., a Snapdragon™ processor from Qualcomm® Technologies, Inc., or an OMAP™ processor from Texas Instruments, Inc. The processor 1452 and accompanying circuitry may be provided in a single socket form factor, multiple socket form factor, or a variety of other formats, including in limited hardware configurations or configurations that include fewer than all elements shown in FIG. 14B.

The processor 1452 may communicate with a system memory 1454 over an interconnect 1456 (e.g., a bus). Any number of memory devices may be used to provide for a given amount of system memory. As examples, the memory 1454 may be random access memory (RAM) in accordance with a Joint Electron Devices Engineering Council (JEDEC) design such as the DDR or mobile DDR standards (e.g., LPDDR, LPDDR2, LPDDR3, or LPDDR4). In particular examples, a memory component may comply with a DRAM standard promulgated by JEDEC, such as JESD79F for DDR SDRAM, JESD79-2F for DDR2 SDRAM, JESD79-3F for DDR3 SDRAM, JESD79-4A for DDR4 SDRAM, JESD209 for Low Power DDR (LPDDR), JESD209-2 for LPDDR2, JESD209-3 for LPDDR3, and JESD209-4 for LPDDR4. Such standards (and similar standards) may be referred to as DDR-based standards and communication interfaces of the storage devices that implement such standards may be referred to as DDR-based interfaces. In various implementations, the individual memory devices may be of any number of different package types such as single die package (SDP), dual die package (DDP) or quad die package (Q17P). These devices, in some examples, may be directly soldered onto a motherboard to provide a lower profile solution, while in other examples the devices are configured as one or more memory modules that in turn couple to the motherboard by a given connector. Any number of other memory implementations may be used, such as other types of memory modules, e.g., dual inline memory modules (DIMMs) of different varieties including but not limited to microDIMMs or MiniDIMMs.

To provide for persistent storage of information such as data, applications, operating systems and so forth, a storage 1458 may also couple to the processor 1452 via the interconnect 1456. In an example, the storage 1458 may be implemented via a solid-state disk drive (SSDD). Other devices that may be used for the storage 1458 include flash memory cards, such as Secure Digital (SD) cards, microSD cards, eXtreme Digital (XD) picture cards, and the like, and Universal Serial Bus (USB) flash drives. In an example, the memory device may be or may include memory devices that use chalcogenide glass, multi-threshold level NAND flash memory, NOR flash memory, single or multi-level Phase Change Memory (PCM), a resistive memory, nanowire memory, ferroelectric transistor random access memory (FeTRAM), anti-ferroelectric memory, magnetoresistive random access memory (MRAM) memory that incorporates memristor technology, resistive memory including the metal oxide base, the oxygen vacancy base and the conductive bridge Random Access Memory (CB-RAM), or spin transfer torque (STT)-MRAM, a spintronic magnetic junction memory based device, a magnetic tunneling junction (MTJ)

based device, a DW (Domain Wall) and SOT (Spin Orbit Transfer) based device, a thyristor based memory device, or a combination of any of the above, or other memory.

In low power implementations, the storage 1458 may be on-die memory or registers associated with the processor 1452. However, in some examples, the storage 1458 may be implemented using a micro hard disk drive (HDD). Further, any number of new technologies may be used for the storage 1458 in addition to, or instead of, the technologies described, such resistance change memories, phase change memories, holographic memories, or chemical memories, among others.

The components may communicate over the interconnect 1456. The interconnect 1456 may include any number of technologies, including industry standard architecture (ISA), extended ISA (EISA), peripheral component interconnect (PCI), peripheral component interconnect extended (PCIx), PCI express (PCIe), or any number of other technologies. The interconnect 1456 may be a proprietary bus, for example, used in an SoC based system. Other bus systems may be included, such as an Inter-Integrated Circuit (I2C) interface, a Serial Peripheral Interface (SPI) interface, point to point interfaces, and a power bus, among others.

The interconnect 1456 may couple the processor 1452 to a transceiver 1466, for communications with the connected devices 1462. The transceiver 1466 may use any number of frequencies and protocols, such as 2.4 Gigahertz (GHz) transmissions under the IEEE 802.15.4 standard, using the Bluetooth® low energy (BLE) standard, as defined by the Bluetooth® Special Interest Group, or the ZigBee® standard, among others. Any number of radios, configured for a particular wireless communication protocol, may be used for the connections to the connected devices 1462. For example, a wireless local area network (WLAN) unit may be used to implement Wi-Fi® communications in accordance with the Institute of Electrical and Electronics Engineers (IEEE) 802.11 standard. In addition, wireless wide area communications, e.g., according to a cellular or other wireless wide area protocol, may occur via a wireless wide area network (WWAN) unit.

The wireless network transceiver 1466 (or multiple transceivers) may communicate using multiple standards or radios for communications at a different range. For example, the computing node 1450 may communicate with close devices, e.g., within about 10 meters, using a local transceiver based on Bluetooth Low Energy (BLE), or another low power radio, to save power. More distant connected devices 1462, e.g., within about 50 meters, may be reached over ZigBee® or other intermediate power radios. Both communications techniques may take place over a single radio at different power levels or may take place over separate transceivers, for example, a local transceiver using BLE and a separate mesh transceiver using ZigBee®.

A wireless network transceiver 1466 (e.g., a radio transceiver) may be included to communicate with devices or services in a cloud (e.g., a cloud 1495) via local or wide area network protocols. The wireless network transceiver 1466 may be a low-power wide-area (LPWA) transceiver that follows the IEEE 802.15.4, or IEEE 802.15.4g standards, among others. The computing node 1450 may communicate over a wide area using LoRaWAN™ (Long Range Wide Area Network) developed by Semtech and the LoRa Alliance. The techniques described herein are not limited to these technologies but may be used with any number of other cloud transceivers that implement long range, low bandwidth communications, such as Sigfox, and other technologies. Further, other communications techniques, such as time-slotted channel hopping, described in the IEEE 802.15.4e specification may be used.

Any number of other radio communications and protocols may be used in addition to the systems mentioned for the wireless network transceiver 1466, as described herein. For example, the transceiver 1466 may include a cellular transceiver that uses spread spectrum (SPA/SAS) communications for implementing high-speed communications. Further, any number of other protocols may be used, such as Wi-Fi® networks for medium speed communications and provision of network communications. The transceiver 1466 may include radios that are compatible with any number of 3GPP (Third Generation Partnership Project) specifications, such as Long Term Evolution (LTE) and 5th Generation (5G) communication systems, discussed in further detail at the end of the present disclosure. A network interface controller (NIC) 1468 may be included to provide a wired communication to nodes of the cloud 1495 or to other devices, such as the connected devices 1462 (e.g., operating in a mesh). The wired communication may provide an Ethernet connection or may be based on other types of networks, such as Controller Area Network (CAN), Local Interconnect Network (LIN), DeviceNet, ControlNet, Data Highway+, PROFIBUS, or PROFINET, among many others. An additional NIC 1468 may be included to enable connecting to a second network, for example, a first NIC 1468 providing communications to the cloud over Ethernet, and a second NIC 1468 providing communications to other devices over another type of network.

Given the variety of types of applicable communications from the device to another component or network, applicable communications circuitry used by the device may include or be embodied by any one or more of components 1464, 1466, 1468, or 1470. Accordingly, in various examples, applicable means for communicating (e.g., receiving, transmitting, etc.) may be embodied by such communications circuitry.

The computing node 1450 may include or be coupled to acceleration circuitry 1464, which may be embodied by one or more artificial intelligence (AI) accelerators, a neural compute stick, neuromorphic hardware, an FPGA, an arrangement of GPUs, an arrangement of xPUs/DPUs/IPU/NPUs, one or more SoCs, one or more CPUs, one or more digital signal processors, dedicated ASICs, or other forms of specialized processors or circuitry designed to accomplish one or more specialized tasks. These tasks may include AI processing (including machine learning, training, inferencing, and classification operations), visual data processing, network data processing, object detection, rule analysis, or the like. These tasks also may include the specific computing tasks for service management and service operations discussed elsewhere in this document.

The interconnect 1456 may couple the processor 1452 to a sensor hub or external interface 1470 that is used to connect additional devices or subsystems. The devices may include sensors 1472, such as accelerometers, level sensors, flow sensors, optical light sensors, camera sensors, temperature sensors, global navigation system (e.g., GPS) sensors, pressure sensors, barometric pressure sensors, and the like. The hub or interface 1470 further may be used to connect the computing node 1450 to actuators 1474, such as power switches, valve actuators, an audible sound generator, a visual warning device, and the like.

In some optional examples, various input/output (I/O) devices may be present within or connected to, the computing node 1450. For example, a display or other output device 1484 may be included to show information, such as sensor readings or actuator position. An input device 1486, such as a touch screen or keypad may be included to accept input. An output device 1484 may include any number of forms of audio or visual display, including simple visual outputs such as binary status indicators (e.g., light-emitting diodes (LEDs)) and multi-character visual outputs, or more complex outputs such as display screens (e.g., liquid crystal display (LCD) screens), with the output of characters, graphics, multimedia objects, and the like being generated or produced from the operation of the computing node 1450. A display or console hardware, in the context of the present system, may be used to provide output and receive input of an computing system; to manage components or services of an computing system; identify a state of a computing component or service; or to conduct any other number of management or administration functions or service use cases.

A battery 1476 may power the computing node 1450, although, in examples in which the computing node 1450 is mounted in a fixed location, it may have a power supply coupled to an electrical grid, or the battery may be used as a backup or for temporary capabilities. The battery 1476 may be a lithium ion battery, or a metal-air battery, such as a zinc-air battery, an aluminum-air battery, a lithium-air battery, and the like.

A battery monitor/charger 1478 may be included in the computing node 1450 to track the state of charge (SoCh) of the battery 1476, if included. The battery monitor/charger 1478 may be used to monitor other parameters of the battery 1476 to provide failure predictions, such as the state of health (SoH) and the state of function (SoF) of the battery 1476. The battery monitor/charger 1478 may include a battery monitoring integrated circuit, such as an LTC4020 or an LTC2990 from Linear Technologies, an ADT7488A from ON Semiconductor of Phoenix Arizona, or an IC from the UCD90xxx family from Texas Instruments of Dallas, TX. The battery monitor/charger 1478 may communicate the information on the battery 1476 to the processor 1452 over the interconnect 1456. The battery monitor/charger 1478 may also include an analog-to-digital (ADC) converter that enables the processor 1452 to directly monitor the voltage of the battery 1476 or the current flow from the battery 1476. The battery parameters may be used to determine actions that the computing node 1450 may perform, such as transmission frequency, mesh network operation, sensing frequency, and the like.

A power block 1480, or other power supply coupled to a grid, may be coupled with the battery monitor/charger 1478 to charge the battery 1476. In some examples, the power block 1480 may be replaced with a wireless power receiver to obtain the power wirelessly, for example, through a loop antenna in the computing node 1450. A wireless battery charging circuit, such as an LTC4020 chip from Linear Technologies of Milpitas, California, among others, may be included in the battery monitor/charger 1478. The specific charging circuits may be selected based on the size of the battery 1476, and thus, the current required. The charging may be performed using the Airfuel standard promulgated by the Airfuel Alliance, the Qi wireless charging standard promulgated by the Wireless Power Consortium, or the Rezence charging standard, promulgated by the Alliance for Wireless Power, among others.

The storage 1458 may include instructions 1482 in the form of software, firmware, or hardware commands to implement the techniques described herein. Although such instructions 1482 are shown as code blocks included in the memory 1454 and the storage 1458, it may be understood that any of the code blocks may be replaced with hardwired circuits, for example, built into an application specific integrated circuit (ASIC).

In an example, the instructions 1482 provided via the memory 1454, the storage 1458, or the processor 1452 may be embodied as a non-transitory, machine-readable medium 1460 including code to direct the processor 1452 to perform electronic operations in the computing node 1450. The processor 1452 may access the non-transitory, machine-readable medium 1460 over the interconnect 1456. For instance, the non-transitory, machine-readable medium 1460 may be embodied by devices described for the storage 1458 or may include specific storage units such as storage devices and/or storage disks that include optical disks (e.g., digital versatile disk (DVD), compact disk (CD), CD-ROM, Blu-ray disk), flash drives, floppy disks, hard drives (e.g., SSDs), or any number of other hardware devices in which information is stored for any duration (e.g., for extended time periods, permanently, for brief instances, for temporarily buffering, and/or caching). The non-transitory, machine-readable medium 1460 may include instructions to direct the processor 1452 to perform a specific sequence or flow of actions, for example, as described with respect to the flowchart(s) and block diagram(s) of operations and functionality depicted above. As used herein, the terms "machine-readable medium" and "computer-readable medium" are interchangeable. As used herein, the term "non-transitory computer-readable medium" is expressly defined to include any type of computer readable storage device and/or storage disk and to exclude propagating signals and to exclude transmission media.

Also in a specific example, the instructions 1482 on the processor 1452 (separately, or in combination with the instructions 1482 of the machine readable medium 1460) may configure execution or operation of a trusted execution environment (TEE) 1490. In an example, the TEE 1490 operates as a protected area accessible to the processor 1452 for secure execution of instructions and secure access to data. Various implementations of the TEE 1490, and an accompanying secure area in the processor 1452 or the memory 1454 may be provided, for instance, through use of Intel® Software Guard Extensions (SGX) or ARM® Trust-Zone® hardware security extensions, Intel® Management Engine (ME), or Intel® Converged Security Manageability Engine (CSME). Other aspects of security hardening, hardware roots-of-trust, and trusted or protected operations may be implemented in the computing node 1450 through the TEE 1490 and the processor 1452.

While the illustrated examples of FIG. 14A and FIG. 14B include example components for a compute node and a computing device, respectively, examples disclosed herein are not limited thereto. As used herein, a "computer" may include some or all of the example components of FIGS. 14A and/or 14B in different types of computing environments. Example computing environments include computing devices (e.g., computers) in a distributed networking arrangement such that particular ones of participating computing devices are heterogenous or homogeneous devices. As used herein, a "computer" may include a personal computer, a server, user equipment, an accelerator, etc., including any combinations thereof. In some examples, distributed networking and/or distributed computing includes any number of such computing devices as illustrated in FIGS. 14A and/or 14B, each of which may include different sub-components, different memory capacities, I/O capabilities, etc. For example, because some implementations of distributed networking and/or distributed computing are associated with particular desired functionality, examples disclosed herein include different combinations of components illustrated in FIGS. 14A and/or 14B to satisfy functional objectives of distributed computing tasks. In some examples, the term "compute node" or "computer" only includes the example processor 1404, memory 1406 and I/O subsystem 1408 of FIG. 14A. In some examples, one or more objective functions of a distributed computing task(s) rely on one or more alternate devices/structure located in different parts of an networking environment, such as devices to accommodate data storage (e.g., the example data storage 1410), input/output capabilities (e.g., the example peripheral device(s) 1414), and/or network communication capabilities (e.g., the example NIC 1420).

In some examples, computers operating in a distributed computing and/or distributed networking environment (e.g., a network) are structured to accommodate particular objective functionality in a manner that reduces computational waste. For instance, because a computer includes a subset of the components disclosed in FIGS. 14A and 14B, such computers satisfy execution of distributed computing objective functions without including computing structure that would otherwise be unused and/or underutilized. As such, the term "computer" as used herein includes any combination of structure of FIGS. 14A and/or 14B that is capable of satisfying and/or otherwise executing objective functions of distributed computing tasks. In some examples, computers are structured in a manner commensurate to corresponding distributed computing objective functions in a manner that downscales or upscales in connection with dynamic demand. In some examples, different computers are invoked and/or otherwise instantiated in view of their ability to process one or more tasks of the distributed computing request(s), such that any computer capable of satisfying the tasks proceed with such computing activity.

In the illustrated examples of FIGS. 14A and 14B, computing devices include operating systems. As used herein, an "operating system" is software to control example computing devices, such as the example compute node 1400 of FIG. 14A and/or the example computing node 1450 of FIG. 14B. Example operating systems include, but are not limited to consumer-based operating systems (e.g., Microsoft® Windows® 10, Google® Android® OS, Apple® Mac® OS, etc.). Example operating systems also include, but are not limited to industry-focused operating systems, such as real-time operating systems, hypervisors, etc. An example operating system on a first compute node may be the same or different than an example operating system on a second compute node. In some examples, the operating system invokes alternate software to facilitate one or more functions and/or operations that are not native to the operating system, such as particular communication protocols and/or interpreters. In some examples, the operating system instantiates various functionalities that are not native to the operating system. In some examples, operating systems include varying degrees of complexity and/or capabilities. For instance, a first operating system corresponding to a first compute node includes a real-time operating system having particular performance expectations of responsivity to dynamic input conditions, and a second operating system corresponding to a second compute node includes graphical user interface capabilities to facilitate end-user I/O.

The instructions 1482 may further be transmitted or received over a communications network using a transmission medium via the wireless network transceiver 466 utilizing any one of a number of wireless local area network (WLAN) transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks. Communications over the networks may include one or more different protocols, such as Institute of Electrical and Electronics Engineers (IEEE) 802.11 family of standards known as Wi-Fi, IEEE 802.16 family of standards, IEEE 802.15.4 family of standards, a Long Term Evolution (LTE) family of standards, a Universal Mobile Telecommunications System (UMTS) family of standards, peer-to-peer (P2P) networks, a next generation (NG)/5th generation (5G) standards among others.

Note that the term "circuitry" as used herein refers to, is part of, or includes hardware components such as an electronic circuit, a logic circuit, a processor (shared, dedicated, or group) and/or memory (shared, dedicated, or group), an Application Specific Integrated Circuit (ASIC), a field-programmable device (FPD) (e.g., a field-programmable gate array (FPGA), a programmable logic device (PLD), a complex PLD (CPLD), a high-capacity PLD (HCPLD), a structured ASIC, or a programmable SoC), digital signal processors (DSPs), etc., that are configured to provide the described functionality. In some embodiments, the circuitry may execute one or more software or firmware programs to provide at least some of the described functionality. The term "circuitry" may also refer to a combination of one or more hardware elements (or a combination of circuits used in an electrical or electronic system) with the program code used to carry out the functionality of that program code. In these embodiments, the combination of hardware elements and program code may be referred to as a particular type of circuitry.

The term "processor circuitry" or "processor" as used herein thus refers to, is part of, or includes circuitry capable of sequentially and automatically carrying out a sequence of arithmetic or logical operations, or recording, storing, and/or transferring digital data. The term "processor circuitry" or "processor" may refer to one or more application processors, one or more baseband processors, a physical central processing unit (CPU), a single- or multi-core processor, and/or any other device capable of executing or otherwise operating computer-executable instructions, such as program code, software modules, and/or functional processes.

Embodiments may be implemented in one or a combination of hardware, firmware, and software. Embodiments may also be implemented as instructions stored on a machine-readable storage device, which may be read and executed by at least one processor to perform the operations described herein. A machine-readable storage device may include any non-transitory mechanism for storing information in a form readable by a machine (e.g., a computer). For example, a machine-readable storage device may include read-only memory (ROM), random-access memory (RAM), magnetic disk storage media, optical storage media, flash-memory devices, and other storage devices and media.

Examples, as described herein, may include, or may operate on, logic or a number of components, such as modules, intellectual property (IP) blocks or cores, or mechanisms. Such logic or components may be hardware, software, or firmware communicatively coupled to one or more processors in order to carry out the operations described herein. Logic or components may be hardware modules (e.g., IP block), and as such may be considered tangible entities capable of performing specified operations and may be configured or arranged in a certain manner. In an example, circuits may be arranged (e.g., internally or with respect to external entities such as other circuits) in a specified manner as an IP block, IP core, system-on-chip (SoC), or the like.

In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine-readable medium. In an example, the software, when executed by the underlying hardware of the module, causes the hardware to perform the specified operations. Accordingly, the term hardware module is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein.

Considering examples in which modules are temporarily configured, each of the modules need not be instantiated at any one moment in time. For example, where the modules comprise a general-purpose hardware processor configured using software; the general-purpose hardware processor may be configured as respective different modules at different times. Software may accordingly configure a hardware processor, for example, to constitute a particular module at one instance of time and to constitute a different module at a different instance of time. Modules may also be software or firmware modules, which operate to perform the methodologies described herein.

An IP block (also referred to as an IP core) is a reusable unit of logic, cell, or integrated circuit. An IP block may be used as a part of a field programmable gate array (FPGA), application-specific integrated circuit (ASIC), programmable logic device (PLD), system on a chip (SoC), or the like. It may be configured for a particular purpose, such as digital signal processing or image processing. Example IP cores include central processing unit (CPU) cores, integrated graphics, security, input/output (I/O) control, system agent, graphics processing unit (GPU), artificial intelligence, neural processors, image processing unit, communication interfaces, memory controller, peripheral device control, platform controller hub, or the like.

ADDITIONAL NOTES & EXAMPLES

Example 1 is a server system for managing communication, the server system comprising: a processor; and a memory device including instructions, which when executed by the processor, cause the processor to perform operations comprising: receiving from a user at a healthcare practice, an electronic request to obtain a medical prior authorization (medPA) for a specialty drug to administer for a patient of the healthcare practice; selecting, using a rules service, a communication pathway to submit the medPA to a healthcare payer from a plurality of communication pathways; and initiating a connection with the healthcare payer using the selected communication pathway.

In Example 2, the subject matter of Example 1 includes, wherein the electronic request to obtain the medPA is encoded in a Hypertext Transfer Protocol (HTTP) message request for prior authorization of a patient treatment.

In Example 3, the subject matter of Example 2 includes, wherein the Hypertext Transfer Protocol (HTTP) message request is an eXtended Markup Language (XML) Simple Object Access Protocol (SOAP) message.

In Example 4, the subject matter of Examples 2-3 includes, wherein the Hypertext Transfer Protocol (HTTP) message request is a Representational State Transfer (REST) message.

In Example 5, the subject matter of Examples 1-4 includes, wherein the electronic request to obtain the medPA includes patient context data.

In Example 6, the subject matter of Example 5 includes, wherein the patient context data is received from a drug prescriber.

In Example 7, the subject matter of Examples 5-6 includes, wherein the patient context data is obtained from a partner system.

In Example 8, the subject matter of Examples 1-7 includes, wherein the rules service is configured using machine learning.

In Example 9, the subject matter of Examples 1-8 includes, wherein the rules service is configured to use a weighted function to sort the plurality of communication pathways.

In Example 10, the subject matter of Example 9 includes, wherein the weighted function includes a recency weight.

In Example 11, the subject matter of Examples 1-10 includes, wherein the rules service is configured to sort the plurality of communication pathways using a plurality of factors.

In Example 12, the subject matter of Example 11 includes, wherein the plurality of factors include one or more of: a time from medPA submission to decision, an amount of data required for the medPA submission, a follow up frequency, a denial rate, an approval rate, an approved as requested rate, a preferred user experience score, a payer discrete response type, or a recency factor.

In Example 13, the subject matter of Examples 11-12 includes, wherein the rules service is configured to sort the plurality of communication pathways in order of a most likely to obtain a timely response to a least likely to obtain a timely response.

In Example 14, the subject matter of Example 13 includes, wherein initiating the connection with the healthcare payer using the selected communication pathway includes iteratively initiating connections with the healthcare payer to obtain the medPA using the sorted plurality of communication pathways.

In Example 15, the subject matter of Example 14 includes, wherein iteratively initiating connections with the healthcare payer comprises: attempting a first connection using a first communication pathway of the sorted plurality of communication pathways; and attempting a second connection using a second communication pathway of the sorted plurality of communication pathways, when the first connection fails, wherein the second communication pathway is ranked lower than the first communication pathway in the sorted plurality of communication pathways.

In Example 16, the subject matter of Examples 1-15 includes, wherein the plurality of communication pathways include at least two of: a business-to-business connection, an application programming interface exposed by the healthcare payer to the server system, a facsimile channel, or a telephone representative.

In Example 17, the subject matter of Examples 1-16 includes, FHIR-based drug format pathway.

In Example 18, the subject matter of Examples 1-17 includes, wherein the medPA is included in a medical benefit verification (medBV) for the specialty drug, and wherein the instructions cause the processor to perform operations comprising: determining whether the medPA is required as a portion of the medBV using machine learning.

Example 19 is a method for managing communication, the method performed at a server system and the method comprising: receiving from a user at a healthcare practice, an electronic request to obtain a medical prior authorization (medPA) for a specialty drug to administer for a patient of the healthcare practice; selecting, using a rules service, a communication pathway to submit the medPA to a healthcare payer from a plurality of communication pathways; and initiating a connection with the healthcare payer using the selected communication pathway.

In Example 20, the subject matter of Example 19 includes, wherein the electronic request to obtain the medPA is encoded in a Hypertext Transfer Protocol (HTTP) message request for prior authorization of a patient treatment.

In Example 21, the subject matter of Example 20 includes, wherein the Hypertext Transfer Protocol (HTTP) message request is an eXtended Markup Language (XML) Simple Object Access Protocol (SOAP) message.

In Example 22, the subject matter of Examples 20-21 includes, wherein the Hypertext Transfer Protocol (HTTP) message request is a Representational State Transfer (REST) message.

In Example 23, the subject matter of Examples 19-22 includes, wherein the electronic request to obtain the medPA includes patient context data.

In Example 24, the subject matter of Example 23 includes, wherein the patient context data is received from a drug prescriber.

In Example 25, the subject matter of Examples 23-24 includes, wherein the patient context data is obtained from a partner system.

In Example 26, the subject matter of Examples 19-25 includes, wherein the rules service is configured using machine learning.

In Example 27, the subject matter of Examples 19-26 includes, wherein the rules service is configured to use a weighted function to sort the plurality of communication pathways.

In Example 28, the subject matter of Example 27 includes, wherein the weighted function includes a recency weight.

In Example 29, the subject matter of Examples 19-28 includes, wherein the rules service is configured to sort the plurality of communication pathways using a plurality of factors.

In Example 30, the subject matter of Example 29 includes, wherein the plurality of factors include one or more of: a time from medPA submission to decision, an amount of data required for the medPA submission, a follow up frequency, a denial rate, an approval rate, an approved as requested rate, a preferred user experience score, a payer discrete response type, or a recency factor.

In Example 31, the subject matter of Examples 29-30 includes, wherein the rules service is configured to sort the plurality of communication pathways in order of a most likely to obtain a timely response to a least likely to obtain a timely response.

In Example 32, the subject matter of Example 31 includes, wherein initiating the connection with the healthcare payer using the selected communication pathway includes iteratively initiating connections with the healthcare payer to obtain the medPA using the sorted plurality of communication pathways.

In Example 33, the subject matter of Example 32 includes, wherein iteratively initiating connections with the healthcare payer comprises: attempting a first connection using a first communication pathway of the sorted plurality of communication pathways; and attempting a second connection using a second communication pathway of the sorted plurality of communication pathways, when the first connection fails, wherein the second communication pathway is ranked lower than the first communication pathway in the sorted plurality of communication pathways.

In Example 34, the subject matter of Examples 19-33 includes, wherein the plurality of communication pathways include at least two of: a business-to-business connection, an application programming interface exposed by the healthcare payer to the server system, a facsimile channel, or a telephone representative.

In Example 35, the subject matter of Examples 19-34 includes, FHIR-based drug format pathway.

In Example 36, the subject matter of Examples 19-35 includes, wherein the medPA is included in a medical benefit verification (medBV) for the specialty drug, and wherein the instructions cause the processor to perform operations comprising: determining whether the medPA is required as a portion of the medBV using machine learning.

Example 37 is a non-transitory machine-readable medium including instructions for managing communication, which when executed by a server system, cause the server system to perform operations comprising: receiving from a user at a healthcare practice, an electronic request to obtain a medical prior authorization (medPA) for a specialty drug to administer for a patient of the healthcare practice; selecting, using a rules service, a communication pathway to submit the medPA to a healthcare payer from a plurality of communication pathways; and initiating a connection with the healthcare payer using the selected communication pathway.

In Example 38, the subject matter of Example 37 includes, wherein the electronic request to obtain the medPA is encoded in a Hypertext Transfer Protocol (HTTP) message request for prior authorization of a patient treatment.

In Example 39, the subject matter of Example 38 includes, wherein the Hypertext Transfer Protocol (HTTP) message request is an eXtended Markup Language (XML) Simple Object Access Protocol (SOAP) message.

In Example 40, the subject matter of Examples 38-39 includes, wherein the Hypertext Transfer Protocol (HTTP) message request is a Representational State Transfer (REST) message.

In Example 41, the subject matter of Examples 37-40 includes, wherein the electronic request to obtain the medPA includes patient context data.

In Example 42, the subject matter of Example 41 includes, wherein the patient context data is received from a drug prescriber.

In Example 43, the subject matter of Examples 41-42 includes, wherein the patient context data is obtained from a partner system.

In Example 44, the subject matter of Examples 37-43 includes, wherein the rules service is configured using machine learning.

In Example 45, the subject matter of Examples 37-44 includes, wherein the rules service is configured to use a weighted function to sort the plurality of communication pathways.

In Example 46, the subject matter of Example 45 includes, wherein the weighted function includes a recency weight.

In Example 47, the subject matter of Examples 37-46 includes, wherein the rules service is configured to sort the plurality of communication pathways using a plurality of factors.

In Example 48, the subject matter of Example 47 includes, wherein the plurality of factors include one or more of: a time from medPA submission to decision, an amount of data required for the medPA submission, a follow up frequency, a denial rate, an approval rate, an approved as requested rate, a preferred user experience score, a payer discrete response type, or a recency factor.

In Example 49, the subject matter of Examples 47-48 includes, wherein the rules service is configured to sort the plurality of communication pathways in order of a most likely to obtain a timely response to a least likely to obtain a timely response.

In Example 50, the subject matter of Example 49 includes, wherein initiating the connection with the healthcare payer using the selected communication pathway includes iteratively initiating connections with the healthcare payer to obtain the medPA using the sorted plurality of communication pathways.

In Example 51, the subject matter of Example 50 includes, wherein iteratively initiating connections with the healthcare payer comprises: attempting a first connection using a first communication pathway of the sorted plurality of communication pathways; and attempting a second connection using a second communication pathway of the sorted plurality of communication pathways, when the first connection fails, wherein the second communication pathway is ranked lower than the first communication pathway in the sorted plurality of communication pathways.

In Example 52, the subject matter of Examples 37-51 includes, wherein the plurality of communication pathways include at least two of: a business-to-business connection, an application programming interface exposed by the healthcare payer to the server system, a facsimile channel, or a telephone representative.

In Example 53, the subject matter of Examples 37-52 includes, FHIR-based drug format pathway.

In Example 54, the subject matter of Examples 37-53 includes, wherein the medPA is included in a medical benefit verification (medBV) for the specialty drug, and wherein the instructions cause the processor to perform operations comprising: determining whether the medPA is required as a portion of the medBV using machine learning.

Example 55 is at least one machine-readable medium including instructions that, when executed by processing circuitry, cause the processing circuitry to perform operations to implement of any of Examples 1-54.

Example 56 is an apparatus comprising means to implement of any of Examples 1-54.

Example 57 is a system to implement of any of Examples 1-54.

Example 58 is a method to implement of any of Examples 1-54.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, also contemplated are examples that include the elements shown or described. Moreover, also contemplated are examples using any combination or permutation of those elements shown or described (or one or more aspects thereof), either with respect to a particular example (or one or more aspects thereof), or with respect to other examples (or one or more aspects thereof) shown or described herein.

Publications, patents, and patent documents referred to in this document are incorporated by reference herein in their entirety, as though individually incorporated by reference. In the event of inconsistent usages between this document and those documents so incorporated by reference, the usage in the incorporated reference(s) are supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to suggest a numerical order for their objects.

The above description is intended to be illustrative, and not restrictive. For example, the above-described examples (or one or more aspects thereof) may be used in combination with others. Other embodiments may be used, such as by one of ordinary skill in the art upon reviewing the above description. The Abstract is to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. However, the claims may not set forth every feature disclosed herein as embodiments may feature a subset of said features. Further, embodiments may include fewer features than those disclosed in a particular example. Thus, the following claims are hereby incorporated into the Detailed Description, with a claim standing on its own as a separate embodiment. The scope of the embodiments disclosed herein is to be determined with reference to the appended claims, along with the full scope of equivalents to which such claims are entitled.

What is claimed is:

1. A server system for managing communication, the server system comprising:
a processor; and
a memory device including instructions, which when executed by the processor, cause the processor to perform operations comprising:
receiving, at a workflow service provided by the server system, from a client application operated by a user at a healthcare practice, an electronic request to obtain a medical prior authorization (medPA) for a specialty drug to administer for a patient of the healthcare practice;
selecting, using a rules service, a communication pathway to submit the medPA to a healthcare payer from a plurality of communication pathways, wherein the rules service is configured to implement a machine-learning model trained using supervised learning on labeled medPA outcome data, the machine-learning model being configured to generate, for each of the plurality of communication pathways, an approval-probability score based on at least (a) a payer-specific historical approval-rate feature and (b) a payer-specific discrete-response-type feature, wherein the rules service selects the communication pathway having the highest approval-probability score as determined by the machine-learning model, and to use a multi-factor evaluation to sort the plurality of communication pathways using at least two of a plurality of factors, wherein the rules service and the workflow service are implemented as micro-services hosted by the server system, and wherein the rules service is instantiated by the workflow service via an application programming interface; and initiating, by the workflow service, a connection with the healthcare payer using the selected communication pathway.

2. The server system of claim 1, wherein the electronic request to obtain the medPA is encoded in a Hypertext Transfer Protocol (HTTP) message request for prior authorization of a patient treatment.

3. The server system of claim 2, wherein the Hypertext Transfer Protocol (HTTP) message request is an extended Markup Language (XML) Simple Object Access Protocol (SOAP) message.

4. The server system of claim 2, wherein the Hypertext Transfer Protocol (HTTP) message request is a Representational State Transfer (REST) message.

5. The server system of claim 1, wherein the electronic request to obtain the medPA includes patient context data.

6. The server system of claim 5, wherein the patient context data is received from a drug prescriber.

7. The server system of claim 5, wherein the patient context data is obtained from a partner system.

8. The server system of claim 1, wherein the rules service is configured using machine learning.

9. The server system of claim 1, wherein the rules service is configured to use a weighted function to sort the plurality of communication pathways.

10. The server system of claim 9, wherein the weighted function includes a recency weight.

11. The server system of claim 1, wherein the plurality of factors include one or more of: a time from medPA submission to decision, an amount of data required for the medPA submission, a follow up frequency, a denial rate, an approval rate, an approved as requested rate, a preferred user experience score, a payer discrete response type, or a recency factor.

12. The server system of claim 1, wherein the rules service is configured to sort the plurality of communication pathways in order of a most likely to obtain a timely response to a least likely to obtain a timely response.

13. The server system of claim 12, wherein initiating the connection with the healthcare payer using the selected communication pathway includes iteratively initiating connections with the healthcare payer to obtain the medPA using the sorted plurality of communication pathways.

14. The server system of claim 13, wherein iteratively initiating connections with the healthcare payer comprises:

attempting a first connection using a first communication pathway of the sorted plurality of communication pathways; and attempting a second connection using a second communication pathway of the sorted plurality of communication pathways, when the first connection fails, wherein the second communication pathway is ranked lower than the first communication pathway in the sorted plurality of communication pathways.

15. The server system of claim 12, wherein a metric to measure whether a response is timely is based on an industry standard.

16. The server system of claim 12, wherein a metric to measure whether a response is timely is based on a type of communication pathway used.

17. The server system of claim 1, wherein the plurality of communication pathways include at least two of: a business-to-business connection, an application programming interface exposed by the healthcare payer to the server system, a facsimile channel, or a telephone representative.

18. The server system of claim 1, wherein the plurality of communication pathways include at least two of: an ANSI X12 EDI 278 transaction set pathway, a National Council for Prescription Drug Programs (NCPDP) communication standard pathway, a robotic process automation (RPA) communication pathway, a facsimile communication pathway, a telephone communication pathway, or a HL7 FHIR-based drug format pathway.

19. The server system of claim 1, wherein the medPA is included in a medical benefit verification (medBV) for the specialty drug, and wherein the instructions cause the processor to perform operations comprising:

determining whether the medPA is required as a portion of the medBV using machine learning.

20. The server system of claim 1, wherein the rules service is configured to sort the plurality of communication pathways according to their respective likelihood of obtaining a final disposition of a prior authentication request.

21. The server system of claim 1, wherein the rules service is configured to sort the plurality of communication pathways according most-likely to lead to a successful prior authorization to a least-likely to lead to a successful prior authorization.

22. A non-transitory machine-readable medium including instructions for managing communication, which when executed by a server system, cause the server system to perform operations comprising:

receiving, at a workflow service provided by the server system, from a client application operated by a user at a healthcare practice, an electronic request to obtain a medical prior authorization (medPA) for a specialty drug to administer for a patient of the healthcare practice;

selecting, using a rules service, a communication pathway to submit the medPA to a healthcare payer from a plurality of communication pathways, wherein the rules service is configured to implement a machine-learning model trained using supervised learning on labeled medPA outcome data, the machine-learning model being configured to generate, for each of the plurality of communication pathways, an approval-probability score based on at least (a) a payer-specific historical approval-rate feature and (b) a payer-specific discrete-response-type feature, wherein the rules service selects the communication pathway having the highest approval-probability score as determined by the machine-learning model, and to use a multi-factor sort process to sort the plurality of communication pathways using at least two of a plurality of factors, wherein the rules service and the workflow service are implemented as microservices hosted by the server system, and wherein the rules service is instantiated by the workflow service via an application programming interface; and initiating, by the workflow service, a connection with the healthcare payer using the selected communication 5 pathway.

23. The non-transitory machine-readable medium of claim 22, wherein the plurality of factors include one or more of: a time from medPA submission to decision, an amount of data required for the medPA submission, a follow 10 up frequency, a denial rate, an approval rate, an approved as requested rate, a preferred user experience score, a payer discrete response type, or a recency factor.

\* \* \* \* \*